(12) United States Patent
Shinohara et al.

(10) Patent No.: US 11,529,509 B2
(45) Date of Patent: Dec. 20, 2022

(54) BLOOD PUMP CONTROLLER AND VENTRICULAR ASSIST SYSTEM

(71) Applicant: SUN MEDICAL TECHNOLOGY RESEARCH CORPORATION, Nagano (JP)

(72) Inventors: Kazuto Shinohara, Nagano (JP); Masahiko Ito, Nagano (JP); Masaaki Hanaoka, Nagano (JP); Nozomi Koike, Nagano (JP); Hiroaki Fujimori, Nagano (JP)

(73) Assignee: SUN MEDICAL TECHNOLOGY RESEARCH CORPORATION, Nagano (JP)

(*) Notice: Subject to any disclaimer, the term of this patent is extended or adjusted under 35 U.S.C. 154(b) by 395 days.

(21) Appl. No.: 16/726,248

(22) Filed: Dec. 24, 2019

(65) Prior Publication Data

US 2020/0206400 A1 Jul. 2, 2020

(30) Foreign Application Priority Data

Dec. 26, 2018 (JP) .............................. JP2018-242272

(51) Int. Cl.
  *A61M 60/871* (2021.01)
  *A61M 60/216* (2021.01)
  (Continued)

(52) U.S. Cl.
  CPC ........ *A61M 60/871* (2021.01); *A61M 60/178* (2021.01); *A61M 60/216* (2021.01);
  (Continued)

(58) Field of Classification Search
  CPC .. A61M 60/178; A61M 60/232; A61M 60/50; A61M 60/508; A61M 60/546;
  (Continued)

(56) References Cited

U.S. PATENT DOCUMENTS

2002/0064973 A1 5/2002 Nakamura et al.
2003/0069465 A1 4/2003 Benkowski et al.
(Continued)

FOREIGN PATENT DOCUMENTS

CN 1613158 A 5/2005
JP 2002-110287 A 4/2002
(Continued)

*Primary Examiner* — Jon Eric C Morales
(74) *Attorney, Agent, or Firm* — Hauptman Ham, LLP

(57) ABSTRACT

Provided is a blood pump controller capable of preventing an operation error in performing a battery exchange with a small-sized and light-weighted configuration and exhibiting high waterproof property. A blood pump controller includes: a controller body for driving a blood pump; a battery pack having a first surface on which an electricity-supply-side battery connection connector is disposed and supplying stored electricity to the controller body; and a battery housing body having a slot which has a second surface on which an electricity-receiving-side battery connection connector is disposed and in which the battery pack is housed and held. When the battery pack is housed in the slot, an electrical connection is made between a pair of the battery connection connectors, the first surface and the second surface opposedly face each other, and a first sealing member provides sealing such that the first sealing member surrounds the pair of battery connection connectors.

8 Claims, 10 Drawing Sheets

(51) Int. Cl.
*A61M 60/178* (2021.01)
*A61M 60/88* (2021.01)

(52) U.S. Cl.
CPC ..... *A61M 60/88* (2021.01); *A61M 2205/8206* (2013.01); *A61M 2205/8262* (2013.01)

(58) Field of Classification Search
CPC .............. A61M 60/585; A61M 60/861; A61M 60/871; A61M 60/08
See application file for complete search history.

(56) References Cited

U.S. PATENT DOCUMENTS

| | | | |
|---|---|---|---|
| 2004/0253867 | A1 | 12/2004 | Matsumoto |
| 2006/0244417 | A1 | 11/2006 | Tsai et al. |
| 2014/0066689 | A1* | 3/2014 | Rainier ................. A61M 60/88 600/16 |

FOREIGN PATENT DOCUMENTS

| | | | |
|---|---|---|---|
| JP | 201515140 | A | 1/2015 |
| JP | 2016501699 | A | 1/2016 |
| WO | 2014107424 | A2 | 7/2014 |

\* cited by examiner

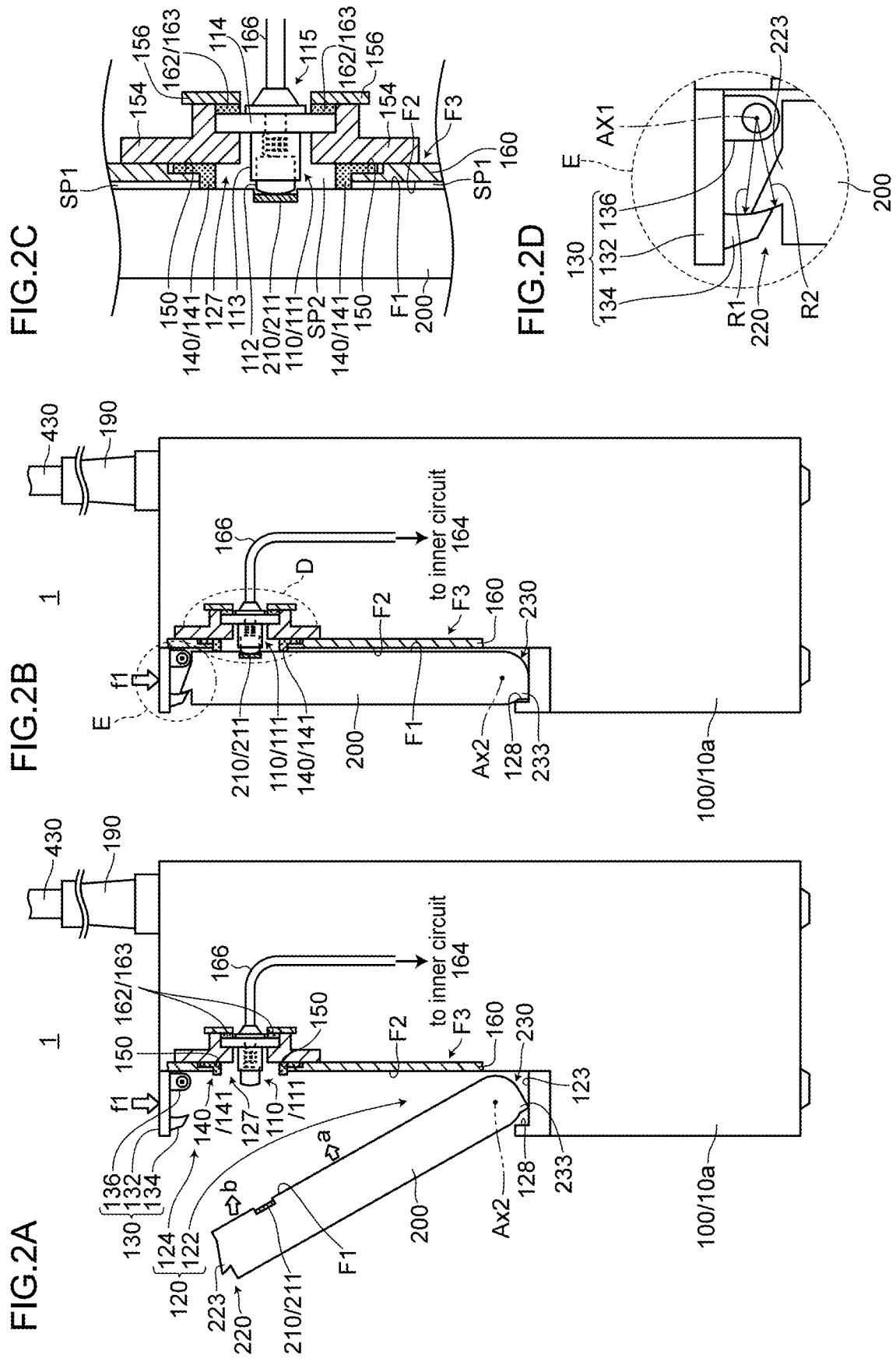

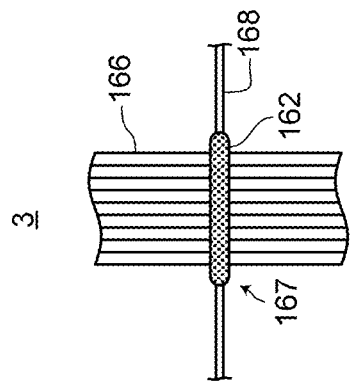
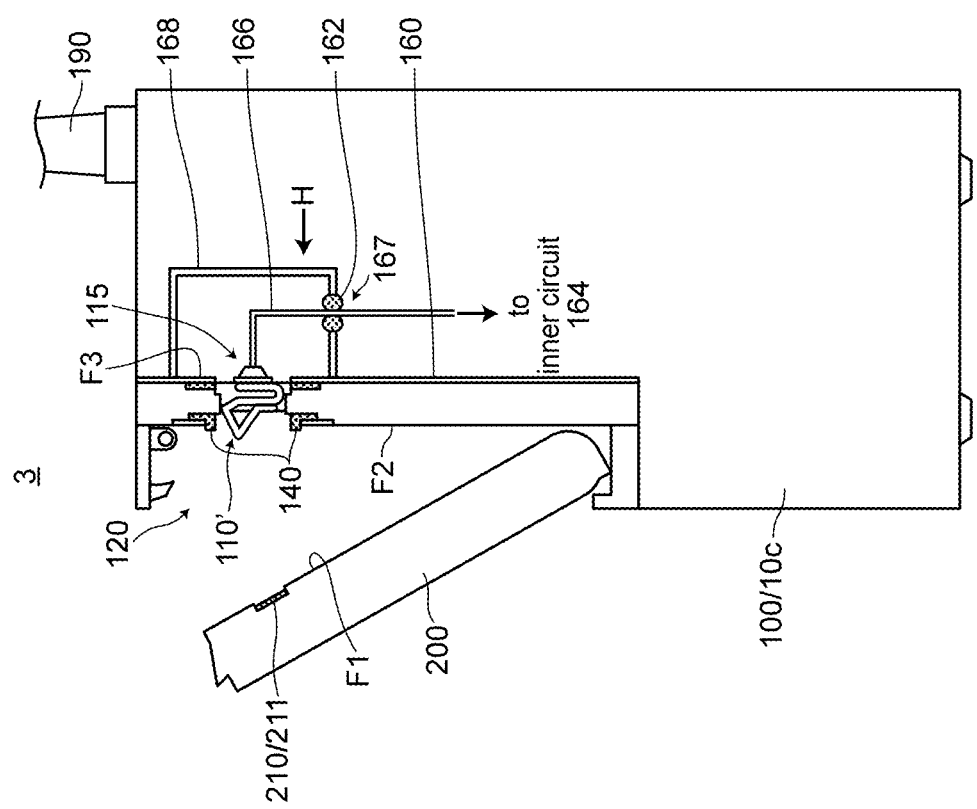

BLOOD PUMP CONTROLLER AND VENTRICULAR ASSIST SYSTEM

RELATED APPLICATIONS

The present application claims priority of Japanese Application Number 2018-242272, filed Dec. 26, 2018, the disclosure of which is hereby incorporated by reference herein in its entirety.

BACKGROUND OF THE INVENTION

1. Field of the Invention

The present invention relates to a blood pump controller and a ventricular assist system.

2. Description of the Related Art

There has been known a ventricular assist system which compensates for a part of a function of a heart as a medical instrument used for a patient suffering from a serious heart malfunction.

FIG. 9 is a view of a conventional blood pump controller 9 and a conventional ventricular assist system 90. As shown in FIG. 9, the ventricular assist system 90 includes: a blood pump 400 embedded in a user 500; artificial blood vessels 410, 420 for connecting a blood flow generated by the blood pump 400 and a blood flow generated by a user's own heart 510; the blood pump controller 9 provided for controlling the blood pump 400 outside a living body; and a drive cable 430 disposed between the blood pump 400 and the blood pump controller 9.

1. Conventional Blood Pump Controller 9

The conventional blood pump controller 9 includes a controller body 910 and a battery pack 920.

The controller body 910 is connected to the blood pump 400 byway of the drive cable 430 and drives the blood pump 400 through the drive cable 430. Slots 912a, 912b which respectively house the battery pack 920 are formed on a back surface of the controller body 910 (on a front side of a sheet on which FIG. 9 is drawn). Two battery connection connectors (a receptacle type, hereinafter referred to as "receptacle-type battery connection connectors") 914 are disposed on an upper surface of the controller body 910.

The battery pack 920 is charged from the outside in a suitable way and stores electricity, and supplies stored electricity to the controller body 910. A battery cable 922 is pulled out from an upper end of the battery pack 920, and battery connection connectors (a plug type, hereinafter referred to as "plug-type battery connection connectors") 924 are disposed on one end of the battery cable 922.

By housing the battery packs 920 in the slots 912a, 912b and by connecting the plug-type battery connection connectors 924 to the receptacle-type battery connection connectors 914, electricity of the battery packs 920 can be supplied to the controller body 910.

In the conventional blood pump controller 9, a so-called round type locking connector is used as the plug-type battery connection connector 924 and the receptacle-type battery connection connector 914. For example, a commercially available connector such as a PL-700 series made by Amphenol Alden or the like is adopted as the plug-type battery connection connector 924 and the receptacle-type battery connection connector 914.

An outer surface of the plug-type battery connection connector 924 and an outer surface of the receptacle-type battery connection connector 914 are covered by a protective cover respectively and hence, once the plug-type battery connection connector 924 and the receptacle-type battery connection connector 914 are connected to each other, the blood pump controller 9 can ensure extremely high waterproof property and dust preventing property.

A barrel 925 of the plug-type battery connection connector 924 is rotatable about an axis of the barrel 925 not shown in the drawing, and a spring force is biased to the barrel 925 in a circumferential direction of the rotatable barrel 925. A protruding key (not shown in the drawing, the same understanding being adopted by the description made hereinafter) is mounted on an inner wall of the barrel 925. A key groove (not shown in the drawing, the same understanding being adopted by the description made hereinafter) is formed on an outer wall of a shell 915 of the receptacle-type battery connection connector 914 in a state where the key groove corresponds to the protruding key.

The plug-type battery connection connector 924 and the receptacle-type battery connection connector 914 are connected to each other in accordance with the following steps, for example.

(1) The plug-type battery connection connector 924 is moved to the position of the receptacle-type battery connection connector 914 (connector positioning step).

(2) An operator rotates and holds the barrel 925 of the plug-type battery connection connector 924 with his fingers against a spring force, and the operator turns his wrist which holds the plug-type battery connection connector 924 about the axis of the barrel 925 and finds the position at which the protruding key of the plug-type battery connection connector 924 is aligned with the key groove of the receptacle-type battery connection connector 914 so that the protruding key starts engagement with the key groove by fitting (connector angle aligning step).

(3) The plug-type battery connection connector 924 is inserted into the receptacle-type battery connection connector 914. At this stage of the operation, the protruding key moves along the key groove in the inserting direction. The insertion of the protruding key is continued until the protruding key arrives at a stopper or a wall (not shown in the drawing) in the inserting direction.

(4) A spring force applied to the barrel 925 is released. At this stage of the operation, the protruding key rotates along a shape of the key groove in the circumferential direction due to the spring force applied to the barrel 925. At a point of time that the barrel 925 rotates to the position where the barrel 925 cannot rotate any more, locking of the connector is completed (connector locking step).

In removing the plug-type battery connection connector 924 from the receptacle-type battery connection connector 914, steps opposite to the above-mentioned steps in order are performed.

The conventional blood pump controller 9 uses the locking connector having the above-mentioned strict locking mechanism and hence, once the plug-type battery connection connector 924 is connected to the receptacle-type battery connection connector 914, the plug-type battery connection connector 924 cannot be removed unless the plurality of steps are taken. Accordingly, the unintended removal of the plug-type battery connection connector 924 can be prevented and the electrical connection can be strictly maintained (high connection reliability being ensured).

SUMMARY OF INVENTION

In general, in a blood pump controller and a ventricular assist system which includes such a blood pump controller, a trouble which occurs in an electrical system may become a cause of a serious accident. In view of such a circumstance, the conventional blood pump controller 9 adopts the above-mentioned locking connector having the strict locking mechanism so as to ensure high connection reliability, high waterproof property, and high dust preventing property. In this case, however, by adopting such a locking connector, it is necessary to arrange the receptacle-type battery connection connectors 914 in the controller body 910 and hence, an extra space for arranging the receptacle-type battery connection connectors 914 becomes necessary. Further, it is necessary to arrange the plug-type battery connection connector 924 on the battery pack 920 in a state where the battery cable 922 is pulled up. That is, the conventional blood pump controller 9 becomes large-sized and increases its weight by a corresponding amount.

In this manner, the conventional blood pump controller 9 has a drawback that it cannot help but to admit large-sizing of the controller and the increase of weight of the controller to compensate for ensuring high connection reliability, waterproof property, and dust preventing property (problems on large sizing and the increase of weight).

Further, in performing connection/removal of connection (releasing) of the plug-type battery connection connector 924 and the receptacle-type battery connection connector 914, cumbersome steps such as the above-mentioned (1) to (4) must be performed so that an operator who performs such steps has to concentrate his attention on his fingertips. Accordingly, depending on a condition of a user 500 himself such as his bad physical condition or a condition of an external environment such as low visibility due to excessively low or high illuminance, there has been a concern that an operation error occurs in a battery exchange. That is, for example, although a user houses the battery packs 920 in the slots 912a, 912b, he forgets to connect the connectors, or although the plug-type battery connection connector 924 is inserted into the receptacle-type battery connection connector 914, the operation does not reach a locking step and hence, a contact between electrodes becomes insufficient.

In an actual operation, even if the above-mentioned operation error occurs, an emergency battery not shown in the drawing is provided as a backup battery and hence, it is possible to continue an operation of the ventricular assist system safely. However, there has been requested a fundamental technique which can prevent the occurrence of the above-mentioned operation error in the battery exchange (problem on an operational error).

2. Connection Structure of Battery Pack of General-Use Electronic Equipment

As one of approaches which can be adopted for preventing an operation error with a simple structure, for example, a technique is also considered where the connection structure of the battery pack of general-use electronic equipment described in JP 2002-110287 A is introduced into a blood pump controller.

FIG. 10A to FIG. 10C are views of the connection structure of a battery pack 820 and a notebook PC 810 described in JP 2002-110287 A. FIG. 10A is a perspective view of the connection structure as viewed from a bottom surface side of the notebook PC 810, FIG. 10B is a perspective view of the connection structure as viewed from an upper surface side of the notebook PC 810, and FIG. 10C is a schematic view of a main part of the connection structure where only a connector portion is shown in an enlarged manner particularly.

As shown in FIG. 10A to FIG. 10C, in the connection structure of the battery pack described in JP 2002-110287 A, a female-side connector 821 and a recessed portion 822 are disposed on the battery pack 820, and a slot 815, a male-side connector 811, and a positioning plate 812 are disposed on the notebook PC 810. In mounting the battery pack 820 in the slot 815, a recessed portion 822 of the battery pack 820 engages with a positioning plate 812 of the notebook PC 810 by fitting engagement while being guided by the positioning plate 812, and the female-side connector 821 is brought into contact with the male-side connector 811 along with such fitting engagement. An electrical connection is made between the battery pack 820 and the notebook PC 810 in this manner.

However, the connection structure of the battery pack described in JP 2002-110287 A is provided by estimating general-use electronic equipment and hence, strict locking is not requested. Accordingly, there is a possibility that the battery pack 820 is removed from the notebook PC 810 unintentionally due to some accident such as vibrations or an impact. Such a structure having a possibility that the electrical connection is unintentionally terminated cannot be directly introduced into a blood pump controller and a ventricular assist system which includes such a blood pump controller.

Further, the connection structure of the battery pack described in JP 2002-110287 A is provided by estimating general-use electronic equipment and hence, it is not safe to say that the connection structure ensures waterproof property necessary for the blood pump controller.

The present invention has been made in view of the above-mentioned circumstances, and it is an object of the present invention to provide a blood pump controller capable of preventing an operation error in performing a battery exchange with a small-sized and light-weighted configuration compared to the conventional blood pump controller and also exhibiting high waterproof property compared to the conventional blood pump controller. It is another object of the present invention to provide a ventricular assist system which includes such a blood pump controller according to the present invention.

[1] A first blood pump controller according to the present invention is a blood pump controller configured to control a blood pump which takes a blood into a pump chamber and supplies the blood taken into the pump chamber into a body of a user by a blood supply mechanism, the first blood pump controller including: a controller body connected to the blood pump byway of a drive cable and configured to drive the blood pump; a battery pack configured to store electricity and to supply stored electricity to the controller body; and a battery housing body having a slot in which the battery pack is housed and held, wherein the controller body is configured to function also as the battery housing body, the battery pack has at least a first surface on which an electricity-supply-side battery connection connector is disposed, the slot has at least a second surface on which an electricity-receiving-side battery connection connector is disposed, the battery pack and the battery housing body are configured such that, in a state where the battery pack is housed in the slot, an electrical connection is made between the electricity-supply-side battery connection connector and the electricity-receiving-side battery connection connector (hereinafter, referred to as "a pair of battery connection connectors"), and the first surface and the second surface oppositely face each other, and a first sealing member is attached to at least either one of the first surface or the second surface and is configured to provide sealing such that the first sealing member surrounds the pair of battery connection connectors in a state where the battery pack is housed in the slot and the first surface and the second surface opposedly face each other.

According to the first blood pump controller of the present invention, when the battery pack is housed in the slot, an electrical connection is made automatically between the electricity-supply-side battery connection connector and the electricity-receiving-side battery connection connector. Accordingly, the battery cable, the plug-type battery connection connector, and the receptacle-type battery connection connector which are used in the conventional blood pump controller become unnecessary. Since these parts become unnecessary, it is possible to provide a small-sized and light-weighted blood pump controller compared to the conventional blood pump controller. Further, in performing a battery exchange, it is unnecessary to take cumbersome steps for connecting the plug-type battery connection connector to the receptacle-type battery connection connector and hence, a battery exchange operation can be simplified. Accordingly, an operation error in performing a battery exchange can be prevented.

When the battery pack is housed in the slot, the pair of battery connection connectors is isolated from the outside by the first sealing member. Accordingly, it is possible to provide the blood pump controller exhibiting high waterproof property compared to the conventional blood pump controller.

[2] A second blood pump controller according to the present invention is a blood pump controller configured to control a blood pump which takes a blood into a pump chamber and supplies the blood taken into the pump chamber into a body of a user by a blood supply mechanism, the second blood pump controller including: a controller body connected to the blood pump byway of a drive cable and configured to drive the blood pump; a battery pack configured to store electricity and to supply stored electricity to the controller body; and a battery housing body having a slot in which the battery pack is housed and held, wherein the controller body and the battery housing body are connected to each other by a given connection cable, the battery pack has at least a first surface on which an electricity-supply-side battery connection connector is disposed, the slot has at least a second surface on which an electricity-receiving-side battery connection connector is disposed, the battery pack and the battery housing body are configured such that, in a state where the battery pack is housed in the slot, an electrical connection is made between the electricity-supply-side battery connection connector and the electricity-receiving-side battery connection connector (hereinafter, referred to as "a pair of battery connection connectors"), and the first surface and the second surface opposedly face each other, and a first sealing member is attached to at least either one of the first surface or the second surface and is configured to provide sealing such that the first sealing member surrounds the pair of battery connection connectors in a state where the battery pack is housed in the slot and the first surface and the second surface opposedly face each other.

According to the second blood pump controller of the present invention, the battery pack and the battery housing body have substantially the same configuration as the battery pack and the battery housing body of the first blood pump controller described in the above [1]. Accordingly, even in the case where the second blood pump controller adopts a mode of "distributed type controller" described later, the second blood pump controller can acquire substantially the same advantageous effects as the advantageous effects acquired by the above-mentioned first blood pump controller.

[3] In the first blood pump controller and the second blood pump controller according to the present invention, it is preferable that either one of the electricity-supply-side battery connection connector or the electricity-receiving-side battery connection connector be formed of a spring type connector having a protruding electrode and a protruding electrode housing portion, and being capable of generating an elastic force which acts against a press fitting force when the protruding electrode is press-fitted in the protruding electrode housing portion, the first sealing member be formed of a first waterproof packing, and assuming a height of the first waterproof packing in a state where a seal pressing force (a pressing force for sealing) is not applied to the first waterproof packing as Hs using the first surface or the second surface to which the first waterproof packing is attached as a reference, assuming a height of a top portion of the protruding electrode in a state where the press fitting force is not applied as H1 using the first surface or the second surface to which the spring type connector is attached as a reference, and assuming a height of the top portion of the protruding electrode or a height of the spring type connector in a state where the top portion of the protruding electrode is brought into a deepest position by pressing by applying the press fitting force as H2 using the first surface or the second surface to which the spring type connector is attached as a reference, the spring type connector and the first waterproof packing be disposed so as to satisfy a relationship of H2<Hs<H1.

In this manner, the relationship of Hs<H1 is satisfied and hence, the protruding electrode of the spring type connector starts contacting with the connector (for example, a planar electrode) on the other side from the position of the height H1. Accordingly, it is possible to ensure a sufficient contact stroke from the position of the height H1 to a predetermined position.

Further, the relationship of H2<Hs is satisfied. Accordingly, for example, even when the first surface of the battery pack is brought into contact with the first waterproof packing of the slot and, immediately thereafter, a force is applied to a second surface side (first waterproof packing side), a stroke which allows the protruding electrode to further enter the protruding electrode housing portion is provided as a surplus and hence, the first surface can be further pressed toward the second surface side (first waterproof packing side) whereby an elastic force of the first waterproof packing can be further applied. As a result, a sealing effect of the first sealing member can be further increased.

[4] In the first blood pump controller and the second blood pump controller according to the present invention, it is preferable that a guide which guides a lower end protruding portion formed on a lower end of the battery pack be disposed on a slot lower portion which forms a lower portion of the slot, and a latching mechanism which engages with an upper end protruding portion formed on an upper end of the battery pack and latches an upper end side of the battery pack be disposed on a slot upper portion which forms an upper portion of the slot.

With such a configuration, the lower end protruding portion of the battery pack is caught by the slot lower portion, and the upper end protruding portion of the battery pack can be latched by the slot upper portion and hence, it is possible to fix and maintain a relative positional relationship between the slot and the battery pack. That is, it is possible to prevent the battery pack from being displaced or removed from the slot.

Further, in the slot, it is possible to prevent both the electrode of the electricity-supply-side battery connection connector and the electrode of the electricity-receiving-side battery connection connector which are brought into contact with each other from being displaced or separated from each other. Further, it is also possible to firmly maintain sealing obtained by the first surface, the second surface, and the first sealing member. Accordingly, it is possible to ensure high connection reliability and high waterproof property.

In such a configuration, "lower" indicates a direction in which gravity is applied when the blood pump controller is placed on a horizontal plane in a normal upright posture, and "upper" indicates a direction opposite to "lower". However, it is not always the case that the blood pump controller is placed in such a posture and hence, "lower" and "upper" are not constrained to the above-mentioned definitions without departing from the gist of the present invention in an actual blood pump controller.

[5] In the first blood pump controller and the second blood pump controller according to the present invention, it is preferable that the battery housing body further include a second sealing member which provides waterproofing between an electrode side of the electricity-receiving-side battery connection connector and an inner circuit disposed in a housing of the battery housing body.

With such a configuration, waterproof property of the inner circuit disposed in the housing of the battery housing body can be further enhanced.

[6] In the blood pump controller described in the above [5], a waterproof partition wall is further disposed in the housing of the battery housing body and is formed so as to surround a portion of the electricity-receiving-side battery connection connector on a housing inner side together with a third surface which is a surface of a case member forming the slot and being disposed on a side opposite to the second surface of the case member, one end of a wiring pattern is connected to the electricity-receiving-side battery connection connector on the housing inner side, the wiring pattern traverses the waterproof partition wall and is connected to the inner circuit, and the second sealing member which provides sealing between the waterproof partition wall and the wiring pattern is disposed in a transverse portion where the wiring pattern traverses the waterproof partition wall.

With such a configuration, also in a mode where the electricity-receiving-side battery connection connector on the housing inner side is surrounded by the waterproof partition wall, waterproof property of the inner circuit is further enhanced by providing the second sealing member.

[7] In the first blood pump controller and the second blood pump controller according to the present invention, in a case where the blood pump controller is operated in a battery drive mode, a cable of an electric system pulled out from the controller body to an outside is only the drive cable.

When the blood pump controller is operated in "battery drive mode" where the blood pump controller is operated using only electricity from the battery pack without connecting an alternating-current (AC)/direct-current (DC) adopter to the blood pump controller, in the conventional blood pump controller, at least two (three in the case where two battery packs are housed) electric system cables including a drive cable and a battery cable which connects the battery pack and the controller body to each other were pulled out from the blood pump controller to the outside.

Accordingly, conventionally for example, there is a concern that an error occurs in removing the cable such as an error where although a user intends to remove the battery cable of one battery pack, the user removes the battery cable of the other battery pack. Further, under an environment where the user has difficulty in viewing the battery pack, there is a concern that a user touches a drive cable although he intends to touch a battery cable.

In the blood pump controller according to the present invention, when the battery pack is housed in the slot, an electric connection is automatically made between the electricity-supply-side battery connection connector and the electricity-receiving-side battery connection connector, and the pair of battery connection connectors are sealed by the first sealing member so that the pair of battery connection connectors are isolated from the outside. Accordingly, it is possible to preferably adopt the configuration where the cable of an electric system which is pulled out from the controller body to the outside is only a drive cable unlike the conventional blood pump controller where the battery cable having one end on which the plug-type battery connection connector is disposed is pulled out from the battery pack.

In this manner, according to the blood pump controller of the present invention, the battery cable and the pair of battery connectors become unnecessary. Accordingly, it is possible to provide the blood pump controller which is small-sized and light-weighted compared to the conventional blood pump controller, and can prevent the occurrence of an error in removal of a cable unlike the conventional blood pump controller thus being capable of preventing an operation error in a battery exchange.

[8] A ventricular assist system according to the present invention includes: a blood pump configured to take a blood into a pump chamber and supply the blood taken into the pump chamber into a body of a user by a blood supply mechanism; a drive cable connected to the blood pump; and a blood pump controller connected to the drive cable and configured to control the blood pump, wherein the blood pump controller is the blood pump controller described in any one of the above [1] to [7].

The ventricular assist system according to the present invention has the above-mentioned configuration and hence, the ventricular assist system can acquire substantially the same advantageous effects as the advantageous effects acquired by the blood pump controller described in the above [1] to [7].

BRIEF DESCRIPTION OF DRAWINGS

FIG. 2A to FIG. 2D are views of the blood pump controller 1 according to the embodiment 1;

FIG. 6A and FIG. 6B are views of a blood pump controller 3 according to a modification 1;

DESCRIPTION OF PREFERRED EMBODIMENTS

Hereinafter, a blood pump controller and a ventricular assist system according to the present invention are described with reference to embodiments shown in drawings. The respective drawings are schematic views, and do not always strictly reflect actual sizes.

Embodiment 1

1. Basic Configuration of Blood Pump Controller 1 According to Embodiment 1

Figure 1A:
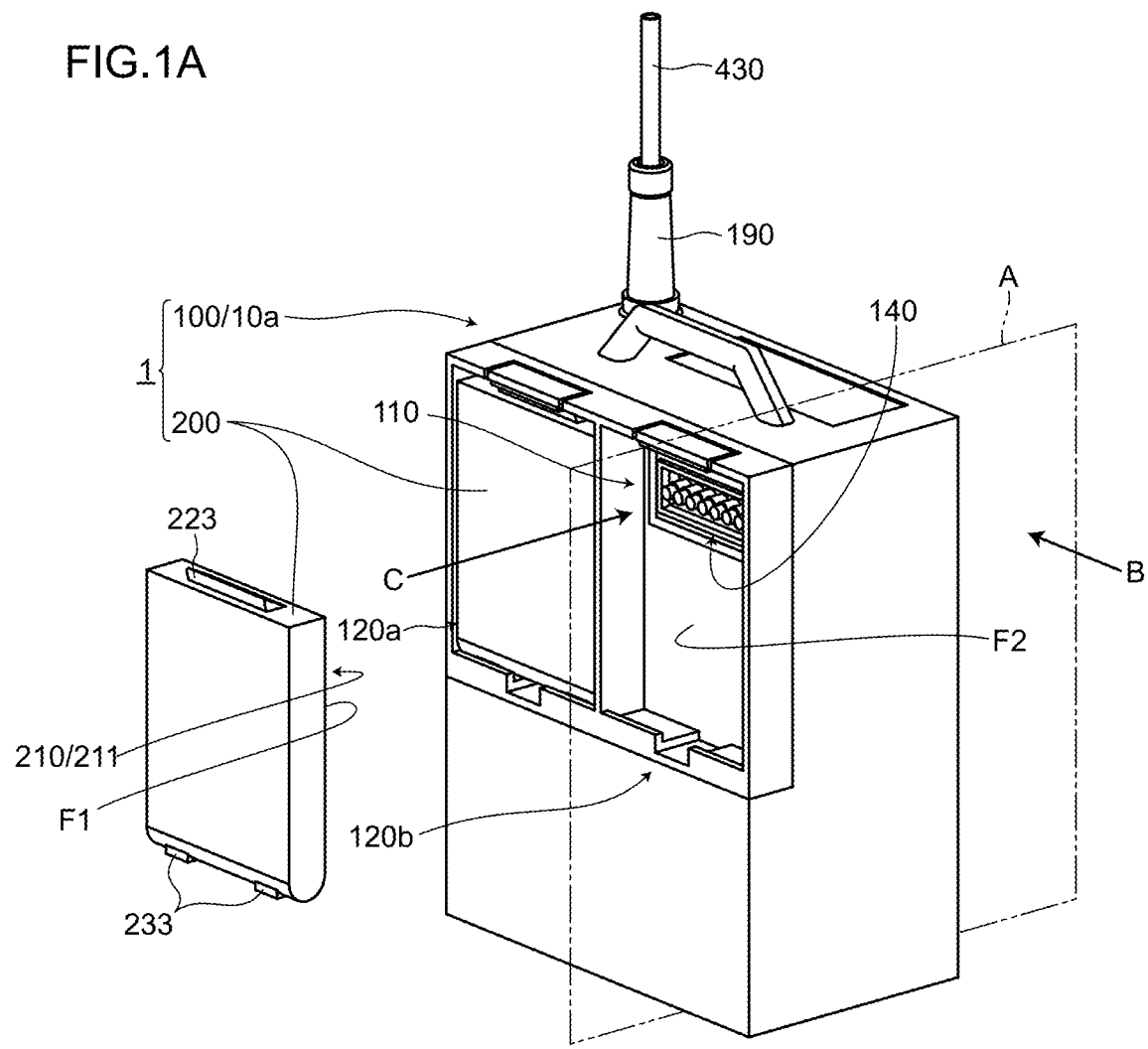
FIG. 1A and FIG. 1B are views of a blood pump controller 1 according to an embodiment 1.
Figure 1B:
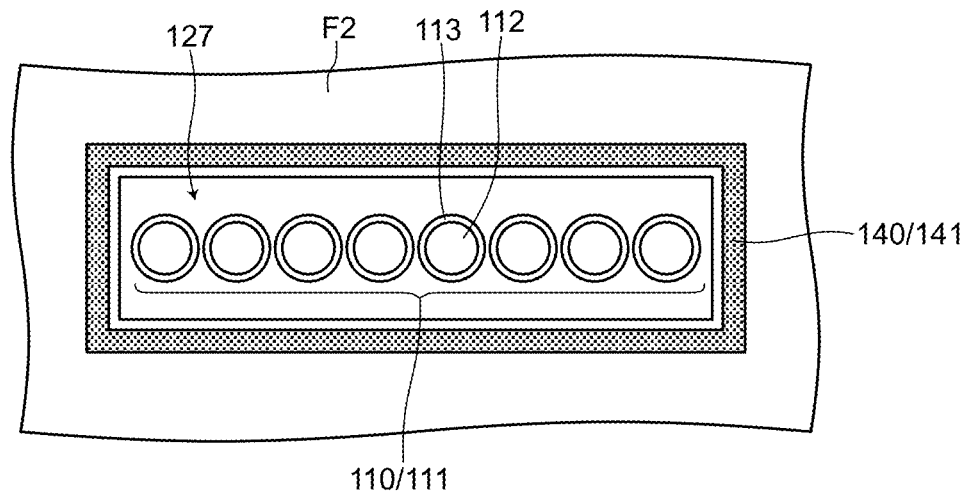

FIG. 1A and FIG. 1B are views of a blood pump controller 1 according to the embodiment 1. FIG. 1A is a perspective view of the blood pump controller 1, and FIG. 1B is a view of an electricity-receiving-side battery connection connector 110 and an area in the vicinity of the electricity-receiving-side battery connection connector 110 as viewed in a direction indicated by an arrow C shown in FIG. 1A.

FIG. 2A to FIG. 2D are views of the blood pump controller 1 according to the embodiment 1. FIG. 2A and FIG. 2B are cross-sectional views of the blood pump controller 1 taken along a plane A shown in FIG. 1A and as viewed in a direction indicated by an arrow B shown in FIG. 1A. FIG. 2A shows a state where a battery pack 200 is about to be housed in a slot 120, and FIG. 2B shows a state where housing of the battery pack 200 in the slot 120 is finished. FIG. 2C is an enlarged cross-sectional view of a main part which is a region surrounded by a broken line D in FIG. 2B. FIG. 2D is an enlarged cross-sectional view of a main part which is a region surrounded by a broken line E in FIG. 2B. A case member 160 which forms the slot 120 is depicted in a mode where only a main part of the case member 160 which becomes necessary for the description is depicted with oblique hatching and a thickness of the case member 160 is depicted in an exaggerating manner. The description of the thickness is omitted with respect to other portions of the case member 160 (the above understanding of the case member 160 being also applicable to other drawings).

(1) Basic Functions and Basic Configuration of Controller

The blood pump controller 1 is, although the detailed illustration of the internal structure of a blood pump 400 is omitted, a controller which controls the blood pump 400 which takes a blood into a pump chamber and supplies the blood taken into the pump chamber into a body of a user 500 by a blood supply mechanism (for example, an impeller or the like) (see FIG. 5 described later).

As shown in FIG. 1A, the blood pump controller 1 includes a controller body 100, a battery pack 200, and a battery housing body 10a. In the blood pump controller 1 according to the embodiment 1, the controller body 100 also functions as the battery housing body 10a. That is, in the description made in the embodiment 1, "controller body 100" can be read as "battery housing body 10a", and "battery housing body 10a" can be read as "controller body 100".

(2) Controller Body 100

The controller body 100 is connected to the blood pump 400 by way of a drive cable 430, and drives the blood pump 400 through the drive cable 430 (see also FIG. 5 described later).

Although the detailed illustration is omitted, the "drive cable 430" includes a power source line for supplying electricity to a motor or the like for driving the blood pump 400. The drive cable 430 may also include a control line for a control. Further, in the drive cable 430, a liquid circulation tube for a cooling seal liquid or the like may be disposed parallel to these electric-system lines. In this specification, the entirety of the electric-system lines, the liquid circulation tube and the like which are formed into a bundle is referred to as "drive cable 430".

(3) Battery Pack 200

The battery pack 200 is charged from the outside in a suitable way and stores electricity, and supplies stored electricity to the controller body 100. To be more specific, the battery pack 200 is formed of a casing in which battery cells and/or a plurality of batteries are housed. In the battery pack 200, a power source control circuit, a monitoring circuit, an LED display circuit and the like may be disposed.

The battery pack 200 has at least a first surface F1 on which an electricity-supply-side battery connection connector 210 is disposed.

In this embodiment, the "first surface F1" is one of main surfaces which form the casing of the battery pack 200. Although the electricity-supply-side battery connection connector 210 is disposed on a portion of the first surface F1 as described above, it is unnecessary that a contact surface of an electrode of the electricity-supply-side battery connection connector 210 (a connecting point of the electrode with the electricity-receiving-side battery connection connector 110) is disposed completely on the same plane as the first surface F1. For example, the electricity-supply-side battery connection connector 210 (planar electrode 211) may be displaced at a position slightly deeper than the plane of the first surface F1 toward the inside of the battery pack 200 (see also FIG. 2A).

(4) Battery Housing Body 10a

The battery housing body 10a has slots 120a, 120b in which the battery pack 200 is housed and held respectively. In the embodiment 1, the battery housing body 10a includes two slots (120a, 120b) and can house two battery packs 200 having the same specification.

Each of the slots 120a, 120b has at least a second surface F2 on which the electricity-receiving-side battery connection connector 110 is disposed.

In this embodiment, the "second surface F2" is one of main surfaces which form each of the slots 120a, 120b. As described above, the electricity-receiving-side battery connection connector 110 is disposed on a portion of the second surface F2. However, it is unnecessary that an electrode of the electricity-receiving-side battery connection connector 110 (connecting point of the electrode with the electricity-supply-side battery connection connector 210) be disposed completely on the same plane as the second surface F2 (see also FIG. 2A). The heights of electrodes are described later.

(5) Electrical Connection

The electricity-supply-side battery connection connector 210 is a connector on an electricity supply side. Although the electricity-supply-side battery connection connector 210 is disposed on a back side so that the electricity-supply-side battery connection connector 210 is not shown in FIG. 1A, the electricity-supply-side battery connection connector 210 may be formed of the planar electrode 211, for example (see also FIG. 2A). The electricity-receiving-side battery connection connector 110 is a connector on an electricity receiving side, and may be formed of a spring type connector 111 having a pin-probe-shaped electrode, for example. The combination of the electricity-supply-side battery connection connector 210 and the electricity-receiving-side battery connection connector 110 is referred to as "a pair of battery connection connectors". Electricity can be supplied from the battery pack 200 to the controller body 100 by connecting the electricity-supply-side battery connection connector 210 and the electricity-receiving-side battery connection connector 110 to each other.

The pair of battery connection connectors may respectively adopt a connector having eight pins (eight electrodes), for example. FIG. 1B shows the electricity-receiving-side battery connection connector 110 in a mode where eight pin-probe-shaped protruding electrodes 112 are arranged in a row. Among eight pins arranged in this manner, three pins disposed on one end side in the arrangement may be allocated as plus terminals of a direct current (DC), three pins disposed on the other end side in the arrangement may be allocated as minus terminals of a DC, and remaining two pins on a center side may be allocated as communication terminals for transmission and reception of signals between the battery pack 200 and the controller body 100. In this embodiment, the battery pack 200 has a function of grasping and controlling its own state. Through the communication using the above-mentioned communication terminals, the battery pack 200 transmits information such as an identifying number, a LOT number, a voltage which can be outputted at present, and the number of times of charging and discharging of the battery to the controller body 100.

The battery pack 200 and the battery housing body 10a are configured such that, when the battery pack 200 is housed in the slot 120a, 120b, the electrical connection is made between the electricity-supply-side battery connection connector 210 and the electricity-receiving-side battery connection connector 110 (see also FIG. 2B). That is, with a simple operation conducted by a user 500 to house the battery pack 200 into the slot 120a, 120b, even when an electrical connection work is not particularly performed, the electrical connection between the battery pack 200 and the controller body 100 is automatically made behind the battery pack 200 so that electricity can be supplied to the controller body 100.

(6) First Sealing Member 140

As shown in FIG. 2A and FIG. 2B, the battery pack 200 and the battery housing body 10a are configured such that the first surface F1 and the second surface F2 opposedly face each other when the battery pack 200 is housed in the slot 120a, 120b.

As shown in FIG. 2B and FIG. 2C, a first sealing member 140 is attached to at least one of the first surface F1 and the second surface F2. The first sealing member 140 is configured to provide sealing such that the first sealing member 140 surrounds the pair of battery connection connectors 110, 210 when the battery pack 200 is housed in the slot 120a, 120b and the first surface F1 and the second surface F2 opposedly face each other.

In this embodiment 1, the first sealing member 140 (first waterproof packing 141) which is disposed so as to surround the electricity-receiving-side battery connection connector 110 is attached to the second surface F2 of the slot 120a, 120b (see also FIG. 1B).

Although the first sealing member 140 (first waterproof packing 141) may be formed of any member provided that the predetermined manner of operation and the predetermined advantageous effects can be acquired, the first sealing member 140 (first waterproof packing 141) may be formed of a member which is made of a resin as a main material, for example.

In the above-mentioned configuration, "so as to surround" means that the first sealing member 140 (first waterproof packing 141) surrounds the pair of battery connection connectors (the electricity-supply-side battery connection connector 210 and the electricity-receiving-side battery connection connector 110) when the first surface F1 and/or the second surface F2 are viewed in a plan view.

In cooperation with the first surface F1 and the second surface F2, the first sealing member 140 provides sealing between an inner region sp2 surrounded by the first sealing member 140 and an outer region sp1 on a side opposite to the inner region sp2 as viewed from the first sealing member 140 thus interrupting an incoming and outgoing flow of a liquid between the inner region sp2 and the outer region sp1 (see symbols sp1, sp2 in FIG. 2C). In this manner, the first sealing member 140 functions as a member which enhances waterproof property of the pair of battery connection connectors.

2. Detailed Configuration of Blood Pump Controller 1 According to Embodiment 1

(1) Opening Portion 127 of Case Member 160

The opening portion 127 is formed in the case member 160 (for example, a rear case member of the controller body 100) which forms the slot 120. Assuming a surface of the case member 160 on a side opposite to the second surface F2 as a third surface F3, a packing groove 150 in which the first sealing member 140 or the first waterproof packing 141 is placed is formed on a third surface F3 side of the case member 160 in the vicinity of the opening portion 127 (see FIG. 2C).

(2) Detailed Structure Around Electricity-Receiving-Side Battery Connection Connector 110

The electricity-receiving-side battery connection connector 110 is, as shown in FIG. 2C in detail, formed of the "spring type connector 111" having protruding electrodes 112 and protruding electrode housing portions 113, and being capable of generating an elastic force which acts against a press fitting force when the protruding electrodes 112 are press-fitted in the protruding electrode housing portions 113. The spring type connector 111 includes: plunger type electrodes (not indicated by a symbol) which form the protruding electrodes 112; plunger barrels (not indicated by a symbol) which form the protruding electrode housing portions 113; spring coils (not indicated by a symbol) which form an elastic member; and an insulating plate member (not indicated by a symbol) to which the plunger barrels are fixed.

The spring type connector 111 is held on a connector holder 154 in a state where the spring type connector 111 is fitted in the connector holder 154 from a rear side (a right side of a sheet on which FIG. 2A to FIG. 2C are drawn) of the connector holder 154.

The connector holder 154 on which the spring type connector 111 is held is fixed to the case member 160 at the opening portion 127 such that the first sealing member 140 or the first waterproof packing 141 (described in detail later) which is placed in the packing groove 150 is sandwiched between the case member 160 and the connector holder 154. In such a configuration, the plunger barrel which forms the protruding electrode housing portion 113 is positioned in the opening portion 127 of the case member 160, and a distal end of the plunger type electrode which forms the protruding electrode 112 appears on a front side (a second surface F2 side or a left side of the sheet on which FIG. 2A to FIG. 2C are drawn) of the case member 160 (see FIG. 2A to FIG. 2C).

A portion 115 of the spring type connector 111 on a housing inner side is connected to a wiring pattern 166 by soldering or the like, for example. This wiring pattern 166 is connected to an inner circuit 164.

The protruding electrode 112 of the spring type connector 111 is connected in a contact manner with the electricity-supply-side battery connection connector 210 of the battery pack 200 which forms a counterpart on the second surface F2 side of the case member 160 which forms the slot 120.

The battery housing body 10*a* further includes a second sealing member 162 which provides waterproofing between an electrode side of the electricity-receiving-side battery connection connector 110 and the inner circuit 164 disposed in the housing of the battery housing body 10*a*.

To be more specific, a second waterproof packing 163 which forms the second sealing member 162 is mounted in a sandwiched manner between a connector pressing member 156 and an insulating plate member 114 to which the plunger barrel is fixed, and provides waterproofing between a plunger type electrode side which is a protruding electrode 112 side and the inner circuit 164 disposed in the housing (see FIG. 2A to FIG. 2C).

(3) Detailed Structure of First Sealing Member 140 and Area in the Vicinity of First Sealing Member 140

In the embodiment 1, the first sealing member 140 is formed of the first waterproof packing 141. The first waterproof packing 141 is formed in a ring shape. The first waterproof packing 141 has a thickness portion (not indicated by a symbol) which is brought into contact with the first surface F1 of the battery pack 200 on an inner side of the ring-shaped first waterproof packing 141, and has a flange portion (not indicated by a symbol) which is continuously formed with the thickness portion on an outer side of the ring-shaped first waterproof packing 141 (see FIG. 1B, FIG. 2C and the like). It is desirable that a thickness of the flange portion be set slightly larger than a depth of the previously mentioned packing groove 150.

The first waterproof packing 141 is attached to the case member 160 in a state where the flange portion is placed in the packing groove 150, the thickness portion extends beyond the opening portion 127 and appears on a front side (second surface F2 side) of the case member 160.

In such a configuration, the second sealing member 162 or the second waterproof packing 163 and the connector holder 154 are pressed by the connector pressing member 156 toward a direction of the case member 160 (in a direction toward the left side of the sheet on which FIG. 2C is drawn). As a result of such pressing, the connector holder 154 presses the first sealing member 140 or the first waterproof packing 141 toward a direction of the case member 160 (in the direction toward the left side of the sheet on which FIG. 2C is drawn).

In this manner, the second sealing member 162 or the second waterproof packing 163 and the first sealing member 140 or the first waterproof packing 141 are collapsed by pressing in a direction perpendicular to the surfaces (the second surface F2 and/or the third surface F3) of the case member 160 thus allowing the structure to exhibit a sealing effect.

As described above, the first sealing member 140 (the first waterproof packing 141) is attached to the second surface F2 of the slot 120*a*, 120*b* such that the first sealing member 140 surrounds the electricity-receiving-side battery connection connector 110 (see FIG. 1B and FIG. 2A to FIG. 2C).

(4) Height Relationship Between Electricity-Receiving-Side Battery Connection Connector 110 and First Sealing Member 140

Figure 3A:
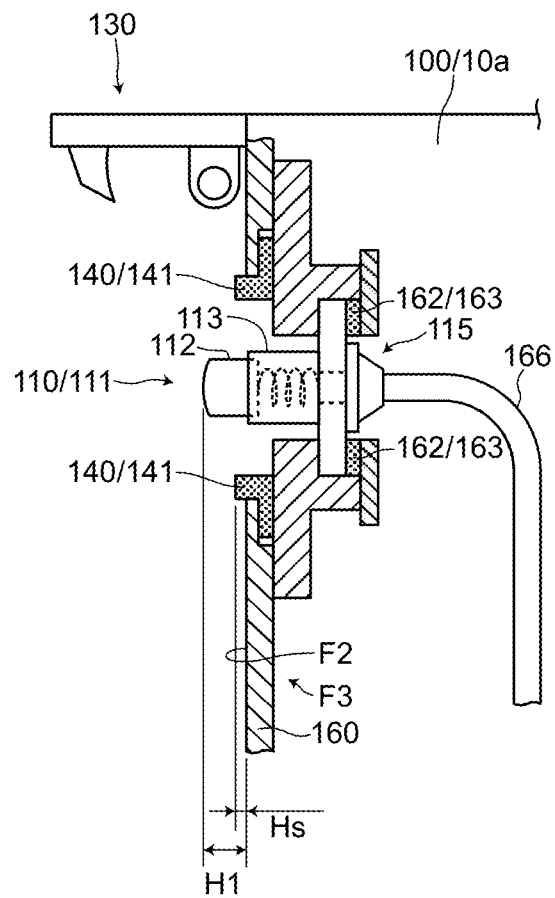
FIG. 3A and FIG. 3B are cross-sectional views of an electricity-receiving-side battery connection connector 110 (spring type connector 111) and a first sealing member 140 (first waterproof packing 141) for describing a height relationship between the electricity-receiving-side battery connection connector 110 and the first sealing member 140.
Figure 3B:
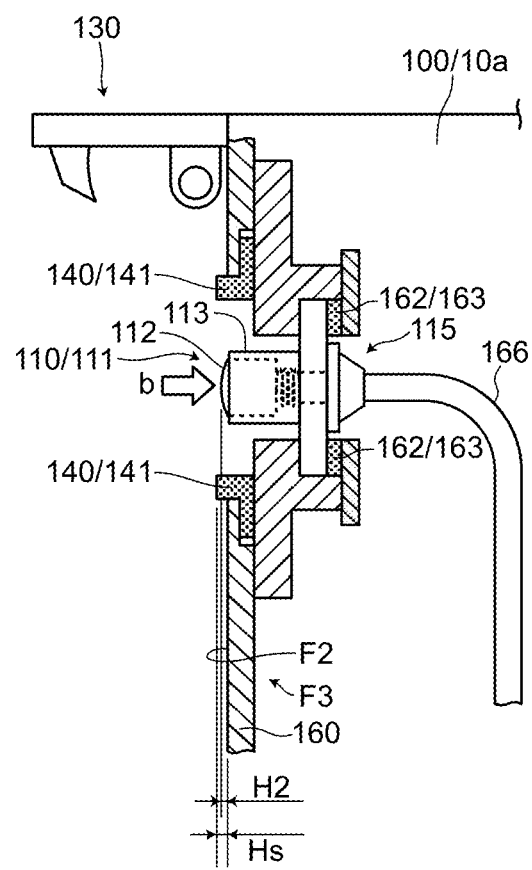

FIG. 3A and FIG. 3B are cross-sectional views of the electricity-receiving-side battery connection connector 110 (spring type connector 111) and the first sealing member 140 (first waterproof packing 141) for describing the height relationship between the electricity-receiving-side battery connection connector 110 and the first sealing member 140. FIG. 3A shows a state where a press fitting force is not applied to the protruding electrode 112, and FIG. 3B shows a state where a press fitting force is applied to the protruding electrode 112 so that a top portion of the protruding electrode 112 is brought into a deepest position on a protruding electrode housing portion 113 side by pressing.

As shown in FIG. 3A and FIG. 3B, using the second surface F2 to which the first waterproof packing 141 is attached as a reference, assume a height of the first waterproof packing 141 in a state where a seal pressing force (a pressing force for sealing) is not applied to the first waterproof packing 141 as Hs. Also using the second surface F2 to which the spring type connector 111 is attached as a reference, assume a height of the top portion of the protruding electrode 112 in a state where a press fitting force is not applied as H1. Further, using the second surface F2 to which the spring type connector 111 is attached as a reference, assume a height of the top portion of the protruding electrode 112 or the height of the spring type connector 111 when the top portion of the protruding electrode 112 is brought into a deepest position by pressing by applying a press fitting force as H2.

In this case, in the blood pump controller 1 according to the embodiment 1, the spring type connector 111 and the first waterproof packing 141 are disposed so as to satisfy a relationship of H2<Hs<H1.

In FIG. 1A, FIG. 1B, FIG. 3A, and FIG. 3B, the case is exemplified where both the spring type connector 111 and the first waterproof packing 141 are disposed on the second surface F2. However, the embodiment 1 is not limited to such a case. In studying the relationship of H2<Hs<H1, the spring type connector 111 may be applied to either the electricity-supply-side battery connection connector 210 or the electricity-receiving-side battery connection connector 110. In other words, the spring type connector 111 may be disposed either on the first surface F1 or the second surface F2. Further, the first waterproof packing 141 may be attached to either the first surface F1 or the second surface F2.

(5) Mechanism for Positioning and Locking Battery Pack 200

Returning to FIG. 2A to FIG. 2D, the mechanism for positioning and locking the battery pack 200 is described.

A guide 128 which guides a lower end protruding portion 233 formed on a lower end 230 of the battery pack 200 is disposed on a slot lower portion 122 which forms a lower portion of the slot 120.

To be more specific, the guide 128 is configured such that a projection portion (not indicated by a symbol) capable of catching the lower end protruding portion 233 of the battery pack 200 and a recessed portion (not indicated by a symbol) surrounded by the projection portion and the second surface F2 of the slot 120 function as guides.

On the other hand, the lower end 230 of the battery pack 200 is formed in a circular arcuate shape having its center on a second axis AX2 when the battery pack 200 is viewed in a cross-sectional view (see FIG. 2A FIG. 2B).

A latching mechanism 130 is disposed on a slot upper portion 124 which forms an upper portion of the slot 120. The latching mechanism 130 engages with an upper end protruding portion 223 formed on an upper end 220 of the battery pack 200 and latches an upper end 220 side of the battery pack 200 (see FIG. 2A).

To be more specific, the lathing mechanism 130 has: a latching pawl 134 which engages with the upper end protruding portion 223 of the battery pack 200; a lever 132 which is a lever for allowing an operator to perform a latching releasing operation with his fingers, is connected to the latching pawl 134, and rotates about a first axis AX1; and a latching spring 136 having one end which is connected to the lever 132 and the other end which is connected to a slot 120 body side for generating a latching holding force.

The following relationships are taken between the respective portions when the battery pack 200 is housed in the slot 120.

(a) When the lower end protruding portion 233 of the battery pack 200 is caught by the projection portion, a state is brought about where the lower end 230 having a circular arcuate shape is naturally placed into the recessed portion, and the lower end 230 having a circular arcuate shape is brought into contact with the recessed portion of the guide 128 (see FIG. 2A).

(b) When the upper end 220 side of the battery pack 200 is pressed in a direction indicated by an arrow b, the lower end 230 having a circular arcuate shape is brought into slide contact with the recessed portion of the guide 128, and the upper end 220 side rotates toward the second surface F2 side of the slot 120 about the second axis AX2 (see FIG. 2A).

(c) When the upper end protruding portion 223 of the battery pack 200 passes the latching pawl 134 of the latching mechanism 130, the upper end protruding portion 223 engages with an inner side of the latching pawl 134 so that latching is completed.

This operation is described in more detail. The inner side of the latching pawl 134 is formed in a circular arcuate shape having a radius R1 about the first axis AX1, and a surface of the upper end protruding portion 223 which engages with the latching pawl 134 is formed in a circular arcuate shape having a radius R2 about the first axis AX1. The radius R1 and the radius R2 are substantially equal or the radius R2 is set slightly smaller than the radius R1. Accordingly, when the upper end protruding portion 223 passes the latching pawl 134 (when the latching pawl 134 gets over the upper end protruding portion 223), the latching pawl 134 is smoothly lowered automatically due to a latching holding force of the latching spring 136 so that the latching pawl 134 engages with the upper end protruding portion 223. Latching is completed at this state.

When latching is completed, there is no possibility that a lower end 230 side of the battery pack 200 is removed to the outside of the slot 120 due to the projection portion of the guide 128. Further, on the upper end 220 side, a biasing force of the latching spring 136 (latching holding force) acts so that the latching pawl 134 is pressed to the upper end protruding portion 223. Accordingly, there is no possibility that latching is easily released.

When the blood pump controller 1 is placed in a normal upright posture in a state where the blood pump controller 1 houses the battery pack 200, a height of the first axis AX1 is below a height of an upper end of the upper end protruding portion 223 of the battery pack 200. Accordingly, the latching pawl 134 strongly engages with the upper end protruding portion 223 and hence, even when the battery pack 220 is displaced in a direction that the latching pawl 134 is instantaneously disengaged due to an impact such as falling, there is no possibility that latching is easily released.

In this manner, the battery pack 200 is positioned and housed in the slot 120, and the positional relationship between the battery pack 200 and the slot 120 is determined and the battery pack 200 is strongly locked (see FIG. 2B and FIG. 2C). (d) When latching is completed and the battery pack 200 is locked in the slot 120, the first surface F1 and the second surface F2 opposedly face each other and an electrical connection is made between the electricity-supply-side battery connection connector 210 and the electricity-receiving-side battery connection connector 110. Along with such an electrical connection, the first sealing member 140 (first waterproof packing 141) which is pressed by being sandwiched by the opposedly facing first surface F1 and second surface F2 is elastically deformed. Accordingly, the first sealing member 140 (first waterproof packing 141) exhibits a sealing effect in cooperation with the first surface F1 and the second surface F2 (see FIG. 2B and FIG. 2C).

The steps of removing the battery pack 200 from the slot 120 are basically opposite to the above-mentioned steps. That is, when the lever 132 is pulled upward, engagement between the latching pawl 134 and the upper end protruding portion 223 is released so that latching is released. When latching is released, due to a reaction force of the pressed first sealing member 140 and a reaction force of the plunger type electrode of the press-fitted spring type connector 111, the battery pack 200 is pushed out from the slot 120a, 120b naturally without requesting a user 500 to pull out the battery pack 200 with a particularly large force, and the removal of the battery pack 200 from the upper end 220 of the battery pack 200 starts.

It is desirable that a latching holding force generated by the latching spring 136 fall within a range of approximately 2N to 3N. When the latching holding force takes a value larger than this range, a latching releasing operation imposes a burden on a physically weak user 500. On the other hand, when the latching holding force takes a value smaller than this range, when a force in a lever releasing direction (a direction opposite to the direction indicated by the arrow b) is slightly strongly applied unintentionally, the force acts in a latching releasing direction and hence, this state is also not desirable.

The guide 128, the latching mechanism 130, the lower end protruding portion 233 and the upper end protruding portion 223 of the battery pack 200 are not limited to a mode shown in the drawings, and these constitutional elements can be embodied in suitable modes.

(6) Electrical Configuration Example

The blood pump controller 1 according to the embodiment 1 may be configured as follows.

The controller body 100 has a blood pump drive part (drive circuit) not shown in the drawing, and an "electrical configuration part" such as a control part for controlling the system. During a period that the user 500 stays in an environment where a commercially available power source is obtainable (to be more specific, a general household, an office or the like where an electrical outlet is disposed), the user 500 connects one connection terminal of an alternating-current (AC)/direct-current (DC) adapter not shown in the drawing to the blood pump controller 1 and, then, connects the other connection terminal of the AC/DC adaptor to the electrical outlet. With such an electrical connection, the blood pump controller 1 can be operated (AC/DC adopter drive mode). In the case where the blood pump controller 1 is operated in an AC/DC adopter drive mode, a required DC power source is generated by an AC/DC adopter (not shown in the drawing), and the DC power source is supplied to the "electrical configuration part". At this stage of operation, the battery pack 200 and an emergency battery (not shown in the drawing) may be charged using a charging circuit not shown in the drawings.

On the other hand, in the case where the user 500 is away from the environment where a commercially available power source is obtainable, the blood pump controller 1 can be operated using electricity of the battery pack 200 incorporated in the blood pump controller 1 (battery drive mode). In the case where the blood pump controller 1 is operated in a battery drive mode, a cable of an electric system pulled out from the controller body 100 to the outside is only the drive cable 430 (see FIG. 1A).

3. Advantageous Effects Acquired by Blood Pump Controller 1 According to Embodiment 1

(1) According to the blood pump controller 1 of the embodiment 1, when the battery pack 200 is housed in the slot 120, an electrical connection is made automatically between the electricity-supply-side battery connection connector 210 and the electricity-receiving-side battery connection connector 110.

Accordingly, the battery cable 922, the receptacle-type battery connection connector 914, and the plug-type battery connection connector 924 which are used in the conventional blood pump controller become unnecessary. Since these parts become unnecessary, it is possible to provide a small-sized and light-weighted blood pump controller compared to the conventional blood pump controller.

Further, in performing a battery exchange, it is unnecessary to take cumbersome steps for connecting the plug-type battery connection connector 924 to the receptacle-type battery connection connector 914 and hence, a battery exchange operation can be simplified. In other words, by merely performing an operation of housing the battery pack 200 in the slot 120, an electrical connection is made automatically between the electricity-supply-side battery connection connector 210 and the electricity-receiving-side battery connection connector 110, and such an electrical connection state is strictly locked. Compared to the conventional blood pump controller, the number of operation actions can be decreased, it is unnecessary for an operator to use his both hands, and it is also unnecessary for the operator to be conscious of the connector connection. That is, the operator can complete a battery exchange without imposing a burden on the user 500 who is a patient without requiring time and efforts. Accordingly, the occurrence of an operation error in performing a battery exchange can be prevented.

When the battery pack 200 is housed in the slot 120, the pair of battery connection connectors (the electricity-supply-side battery connection connector 210 and the electricity-receiving-side battery connection connector 110) is isolated from the outside by the first sealing member 140. Accordingly, it is possible to provide the blood pump controller exhibiting high waterproof property compared to the conventional blood pump controller.

Accordingly, it is possible to provide the blood pump controller capable of preventing an operation error in performing a battery exchange with a small-sized and light-weighted configuration compared to the conventional blood pump controller, and exhibiting high waterproof property compared to the conventional blood pump controller.

(2) In the blood pump controller 1 according to the embodiment 1, assuming the height of the first waterproof packing 141 in a state where a seal pressing force is not applied to the first waterproof packing 141 as Hs, assuming the height of the top portion of the protruding electrode 112 in a state where a press fitting force is not applied when the protruding electrode 112 is press-fitted in the protruding electrode housing portion 113 as H1, and assuming the height of the top portion of the protruding electrode 112 or the height of the spring type connector 111 when the top portion of the protruding electrode 112 is brought into a deepest position by pressing by applying the press fitting force as H2, the spring type connector 111 and the first waterproof packing 141 are disposed so as to satisfy the relationship of H2<Hs<H1.

In this manner, the relationship of Hs<H1 is satisfied and hence, the protruding electrode 112 of the spring type connector 111 starts contacting with the connector on the other side (for example, the planar electrode) from the position of the height H1. Accordingly, it is possible to ensure a sufficient contact stroke from the position of the height H1 to a predetermined position.

Further, the relationship of H2<Hs is satisfied. Accordingly, for example, even when the first surface F1 of the battery pack 200 is brought into contact with the first waterproof packing 141 of the slot 120 and, immediately thereafter, a force is applied to the second surface F2 side (first waterproof packing 141 side), a stroke which allows the protruding electrode 112 to further enter the protruding electrode housing portion 113 is provided as surplus and hence, the first surface F1 can be further pressed toward the second surface F2 side (first waterproof packing 141 side) whereby an elastic force of the first waterproof packing 141 can be further applied. As a result, a sealing effect of the first sealing member 140 can be further increased.

(3) In the blood pump controller 1 according to the embodiment 1, the guide 128 which guides the lower end protruding portion 233 formed on the lower end 230 of the battery pack 200 is disposed on the slot lower portion 122 which forms the lower portion of the slot 120. The latching mechanism 130 is disposed on the slot upper portion 124 which forms the upper portion of the slot 120. The latching mechanism 130 engages with the upper end protruding portion 223 formed on the upper end 220 of the battery pack 200 and latches the upper end 220 side of the battery pack 200.

With such a configuration, the lower end protruding portion 233 of the battery pack is caught by the slot lower portion 122, and the upper end protruding portion 223 of the battery pack 200 can be latched by the slot upper portion 124 and hence, it is possible to fix and maintain a relative positional relationship between the slot 120 and the battery pack 200. That is, it is possible to prevent the battery pack 200 from being displaced or removed from the slot 120.

Further, in the slot 120, it is possible to prevent both the electrodes of the electricity-supply-side battery connection connector 210 and the electrodes of the electricity-receiving-side battery connection connector 110 which are brought into contact with each other from being displaced or separated from each other. Further, it is also possible to firmly maintain sealing obtained by the first surface F1, the second surface F2, and the first sealing member 140. Accordingly, it is possible to ensure high connection reliability and high waterproof property.

(4) In the blood pump controller 1 according to the embodiment 1, the battery housing body 10a further includes the second sealing member 162 which provides waterproofing between the electrode side of the electricity-receiving-side battery connection connector 110 and the inner circuit 164 disposed in the housing of the battery housing body 10a.

Accordingly, waterproof property of the inner circuit 164 disposed in the housing of the battery housing body 10a can be further enhanced.

Embodiment 2

1. Configuration of Blood Pump Controller 2 According to Embodiment 2

Figure 4A:
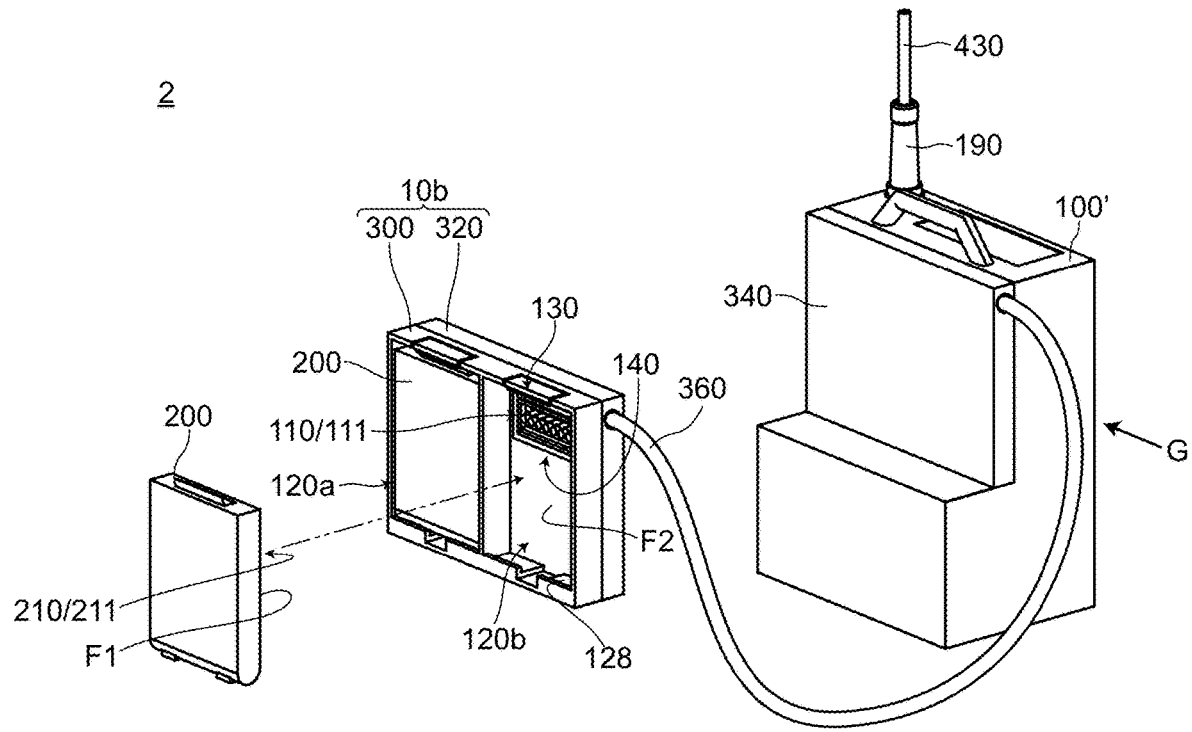
FIG. 4A and FIG. 4B are views of a blood pump controller 2 according to an embodiment 2.
Figure 4B:
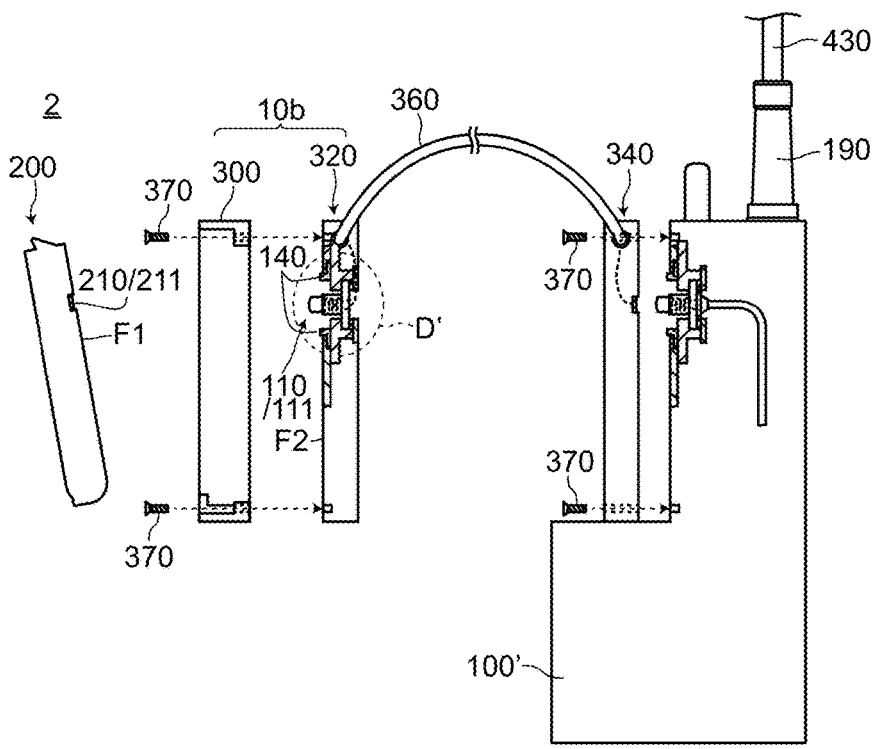

FIG. 4A and FIG. 4B are views of the blood pump controller 2 according to the embodiment 2. FIG. 4A is a perspective view of the blood pump controller 2. FIG. 4B is an exploded view of the blood pump controller 2, and shows a cross section of the blood pump controller 2 taken along a plane (not shown in the drawing) perpendicular to an arrow G shown in FIG. 4A. By standardization and commonalization of parts which are described later, the basic configuration of the region surrounded by a broken line D' is substantially equal to the basic configuration of the region surrounded by the broken line D in FIG. 2B. In the embodiment 2, constitutional elements equal to the corresponding constitutional elements in the embodiment 1 are indicated by the same symbols as the embodiment 1, and the description of the constitutional elements is omitted.

The blood pump controller 2 according to the embodiment 2 basically has substantially the same configuration as the blood pump controller 1 according to the embodiment 1. However, the blood pump controller 2 according to the embodiment 2 differs from the blood pump controller 1 according to the embodiment 1 with respect to a point that a controller body and a battery housing body are provided as separate bodies. Accordingly, the blood pump controller 2 according to the embodiment 2 is described mainly with respect to the difference between the embodiment 1 and the embodiment 2, and other parts which are substantially equal to the corresponding other parts in the embodiment 1 are given the same symbols and the illustration and description of the other parts are omitted.

(1) Distributed Controller

As shown in FIG. 4A, the blood pump controller 2 according to the embodiment 2 includes: a controller body 100' which is connected to a blood pump 400 (see FIG. 5 described later) by way of a drive cable 430 and drives the blood pump 400; battery packs 200 which store electricity and supply stored electricity to the controller body 100'; and a battery housing body 10b in which slots 120a, 120b for housing and holding the battery packs 200 are formed.

The controller body 100' and the battery housing body 10b are formed as separate bodies. From this point of view, the blood pump controller 2 according to the embodiment 2 may be also referred to as a "distributed type controller".

The controller body 100' and the battery housing body 10b are connected by a given connection cable, and electricity is supplied from the battery housing body 10b in which the battery packs 200 are housed to the controller body 100' through an electricity line of the connection cable. The connection cable may include a communication line or the like.

The controller body 100', the battery housing body 10b, and the given connection cable may be provided in any mode. For example, these constitutional elements may be provided in a mode shown in FIG. 4A and FIG. 4B.

That is, the battery housing body 10b may be formed of a battery holder 300 and a battery side attachment 320. The battery holder 300 is formed in a frame shape and holds the batteries. The battery side attachment 320 is integrally assembled to the battery holder 300 by threaded engagement using screws 370 or the like. The battery side attachment 320 has an electricity-receiving-side battery connection connector 110 by which the battery side attachment 320 is connected to the battery pack 200. Further, an attachment connection cable 360 which forms a given connection cable is pulled out from the battery side attachment 320, and the attachment connection cable 360 is connected to a body side attachment 340 (described later).

In this embodiment 2, the slots 120a, 120b are formed by the battery holder 300 and the battery side attachment 320.

Assuming a surface of the battery side attachment 320 on a side where the battery holder 300 is mated to the battery side attachment 320 in assembling the battery housing body 10b as a second surface F2, the electricity-receiving-side battery connection connector 110 is disposed on the second surface F2. Accordingly, when the battery packs 200 are housed in the slots 120a, 120b, an electrical connection is made between the electricity-supply-side battery connection connector 210 and the electricity-receiving-side battery connection connector 110.

A first sealing member 140 is attached to the second surface F2. The first sealing member 140 is formed so as to provide sealing such that the first sealing member 140 surrounds the pair of battery connection connectors (the electricity-supply-side battery connection connector 210 and the electricity-receiving-side battery connection connector 110) in a state where the battery packs 200 are housed in the slots 120a, 120b and the first surfaces F1 of the battery packs 200 and the second surface F2 oppositely face each other.

In the same manner as the embodiment 1, a guide 128 which guides lower end protruding portions 233 formed on lower ends 230 of the battery packs 200 is disposed on a lower side of the inside of a frame of the battery holder 300. In the same manner as the embodiment 1, latching mechanisms 130 which latch upper end 220 sides of the battery packs 200 by engaging with upper end protruding portions 223 formed on upper ends 220 of the battery packs 200 are disposed on an upper side of the inside of the frame of the battery holder 300 (see FIG. 4A).

The above-mentioned attachment connection cable 360 is connected to the body side attachment 340, and the body side attachment 340 is integrally assembled to the controller body 100' by threaded engagement using screws 370 or the like. In a state where the body side attachment 340 is integrated with the controller body 100', an electricity line, a communication line and the like from a group of electrodes of the electricity-receiving-side battery connection connector 110 in the battery side attachment 320 become conductive with the controller body 100' through the attachment connection cable 360. As a result, to consider the blood pump controller 2 as a whole, the battery packs 200 housed in the slots 120 and the controller body 100' are electrically integrally connected to each other.

With respect to (1) the detailed structure of the electricity-receiving-side battery connection connector 110 and an area in the vicinity of the electricity-receiving-side battery connection connector 110, (2) the detailed structure of the first sealing member 140 and an area in the vicinity of the first sealing member 140, (3) the height relationship between the electricity-receiving-side battery connection connector 110 and the first sealing member 140, (4) the mechanism for positioning and locking the battery packs 200 and the like in the battery housing body 10b (the battery holder 300, the battery side attachment 320) of the embodiment 2, the configurations substantially equal to the corresponding configurations of the battery housing body 10a of the above-mentioned embodiment 1 are adopted. Accordingly, also in the battery housing body 10b of the embodiment 2, these configurations acquire substantially the same manner of operation and advantageous effects as the battery housing body 10a of the embodiment 1.

(2) Standardization and Commonalization of Parts

With respect to the constitutional elements which form the slot, standardization and commonalization of parts can be realized by imparting only a function of holding the battery pack 200 to the battery holder 300 while not imparting a function of the electricity-receiving-side battery connection connector to the battery holder 300.

In the case where the controller body is formed as the "distributed type controller" of the embodiment 2, firstly, a part of the controller body 100' which receives electricity, communication and the like has substantially the same structure as the embodiment 1. In this case, a spring type connector having pin-probe-shaped electrodes is disposed (see FIG. 4B). Further, a part of the body side attachment 340 which supplies electricity, communication and the like has substantially the same structure as the electricity-supply-side battery connection connector 210 disposed on the first surface F1 of the battery pack 200. In this case, planar electrodes are disposed. With such a structure, an electrical connection can be made between the body side attachment 340 and the controller body 100'.

On the other hand, in the case where the controller body is formed as the "integral type controller" of the embodiment 1, the battery holder 300 can be used in the controller body. That is, the blood pump controller 1 according to the embodiment 1 can be obtained by integrating the battery holder 300 with the above-mentioned controller body 100' of the embodiment 2 by threadedly engaging the battery holder 300 to the controller body 100' using the screws 370 or the like.

In this manner, by realizing standardization or commonalization of the battery holder 300 or by adopting a common design with respect to (1) the detailed structure of the electricity-receiving-side battery connection connector 110 and an area in the vicinity of the electricity-receiving-side battery connection connector 110, (2) the detailed structure of the first sealing member 140 and an area in the vicinity of the first sealing member 140, (3) the height relationship between the electricity-receiving-side battery connection connector 110 and the first sealing member 140, (4) the mechanism for positioning and locking the battery packs 200 and the like in the controller body 100' and the battery side attachment 320, switching between the "distributed type controller" and the "integral type controller" can be easily performed.

2. Advantageous Effects Acquired by Blood Pump Controller 2 According to Embodiment 2

In the blood pump controller 2 according to the embodiment 2, the controller body 100' and the battery housing body 10b are formed as separate bodies, and these parts are connected to each other by a given connection cable (distributed type controller).

Accordingly, the controller body 100' and the battery housing body 10b which houses the battery packs 200 can be mounted on a right side and a left side of a body of the user 500 in a distributed manner. Alternatively, the controller body 100' and the battery housing body 10b can be also mounted on a back and a chest of the body of the user 500 in a distributed manner. Accordingly, these heavy objects are distributed on left and right sides or on the back and the chest and hence, feeling of weight which user has is reduced whereby the user can improve balancing of his weight in view of increasing a core strength. As a result, the user 500 can more comfortably walk, ride a bicycle, drive an automobile, play golf or the like in a state where the user wears the blood pump controller 2 on his body.

Further, the number of choices whereby the user 500 can suitably use the blood pump controller 1 (integral type controller) according to the embodiment 1 or the blood pump controller 2 (distributed type controller) according to the embodiment 2 to suit a lifestyle of the user 500 is increased. The increase of the number of such choices contributes to the enhancement of quality of life (QOL) of the user 500.

According to the blood pump controller 2 (distributed type controller) of the embodiment 2, in the same manner as the blood pump controller 1 of the embodiment 1, it is possible to provide a blood pump controller capable of preventing an operation error in performing a battery exchange with a small-sized and light-weighted configuration compared to the conventional blood pump controller, and exhibiting high waterproof property compared to the conventional blood pump controller while enjoying the above-mentioned advantageous effects.

The blood pump controller 2 according to the embodiment 2 has substantially the same configuration as the blood pump controller 1 according to the embodiment 1 except for the point that the controller body and the battery housing body are provided as separate bodies. Accordingly, the blood pump controller 2 according to the embodiment 2 directly acquires the corresponding advantageous effects found amongst all advantageous effects which the blood pump controller 1 according to the embodiment 1 acquires.

Embodiment 3

Figure 5:
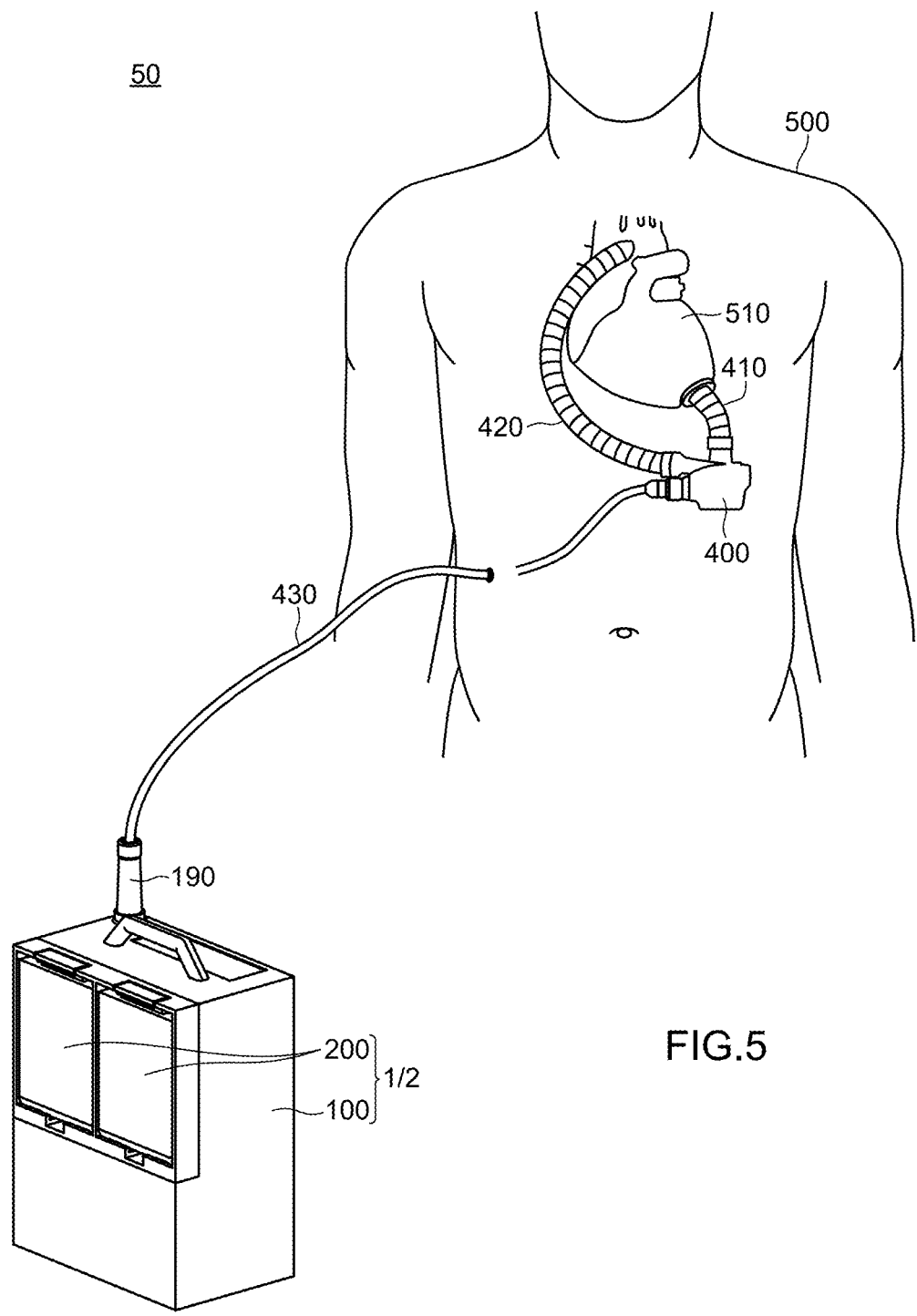
FIG. 5 is a view of a ventricular assist system 50 according to an embodiment 3.

FIG. 5 is a view of a ventricular assist system 50 according to the embodiment 3.

As shown in FIG. 5, the ventricular assist system 50 according to the embodiment 3 includes: a blood pump which takes a blood into a pump chamber and supplies the blood taken into the pump chamber into a body of a user by a blood supply mechanism (detailed illustration of the internal structure of the blood pump 400 being omitted); a drive cable 430 connected to the blood pump 400; and a blood pump controller 1, 2 which is connected to the drive cable 430 and controls the blood pump 400.

The blood pump controller 1, 2 has the configuration of either the blood pump controller 1 according to the embodiment 1 or the blood pump controller 2 according to the embodiment 2.

The ventricular assist system 50 according to the embodiment 3 includes either the blood pump controller 1 according to the embodiment 1 or the blood pump controller 2 according to the embodiment 2. Accordingly, the ventricular assist system 50 according to the embodiment 3 can directly enjoy advantageous effects whereby the blood pump controller can prevent an operation error in performing a battery exchange with a small-sized and light-weighted configuration compared to the conventional blood pump controller, and exhibits high waterproof property compared to the conventional blood pump controller.

[Modifications]

Although the present invention has been described based on the above-mentioned embodiments heretofore, the present invention is not limited to the above-mentioned embodiments. The present invention can be carried out in various modes without departing from the gist of the present invention. For example, the following modifications are also conceivable.

(1) The numbers, the materials, the shapes, the positions, the sizes, and the like of the constitutional elements described in the above-mentioned respective embodiments are provided only for an exemplifying purpose, and these can be changed within ranges where advantageous effects of the present invention are not impaired.

(2) In the respective embodiments, in the housing of the battery housing body 10a, 10b, the connection between the electricity-receiving-side battery connection connector 110 and the inner circuit 164 is described only with respect to the case where the connection is made using the wiring pattern 166. However, the present invention is not limited to such a case.

(2-1) For example, it may be possible to provide a treatment where the connection between the electricity-receiving-side battery connection connector 110 and the inner circuit 164 is surrounded by a waterproof partition wall 168, and the wiring pattern 166 is sealed by a second sealing member 162 (modification 1).

FIG. 6A and FIG. 6B are views of a blood pump controller 3 according to a modification 1. FIG. 6A is a cross-sectional view of the blood pump controller 3, and FIG. 6B is a view of a transverse portion 167 where the wiring pattern 166 traverses the waterproof partition wall 168 as viewed in a direction indicated by an arrow H shown in FIG. 6A. In FIG. 6B, to facilitate the understanding of the transverse portion 167, only a portion of the waterproof partition wall 168 parallel to the arrow H is shown (a portion of the waterproof partition wall 168 perpendicular to the arrow H being not shown in the drawing), and the second sealing member 162 is shown on a front surface side of the waterproof partition wall 168. In FIG. 6A and FIG. 6B, constitutional elements equal to the corresponding constitutional elements in the respective embodiments are indicated by the same symbols as the respective embodiments, and the description of the constitutional elements is omitted.

As shown in FIG. 6A and FIG. 6B, in the blood pump controller 3 according to the modification 1, the waterproof partition wall 168 is further disposed in a housing of a battery housing body 10c. The waterproof partition wall 168 is formed so as to surround a portion 115 of the electricity-receiving-side battery connection connector 110' on a housing inner side together with a third surface F3 which is a surface of a case member 160 forming a slot 120 and being disposed on a side opposite to a second surface F2 of the case member 160. One end of the wiring pattern 166 is connected to the electricity-receiving-side battery connection connector 110' on the housing inner side. The wiring pattern 166 traverses the waterproof partition wall 168 and is connected to the inner circuit 164. The second sealing member 162 is disposed in the transverse portion 167 where the wiring pattern 166 traverses the waterproof partition wall 168. The second sealing member 162 provides sealing between the waterproof partition wall 168 and the wiring pattern 166 by filling a gap between the waterproof partition wall 168 and the wiring pattern 166 with the second sealing member 162.

As "wiring pattern 166", for example, a flat cable, an ordinary cabtyre harness, a PCB or the like can be used. As an example of "traverses", a mode where a hole (not shown in the drawing) is formed in the waterproof partition wall 168 and the wiring pattern 166 passes through the hole or the like is named.

As the electricity-receiving-side battery connection connector 110' shown in FIG. 6A, a leaf-spring-like connector is adopted. The electricity-receiving-side battery connection connector 110' is also a kind of the spring type connector 111 and includes: a leaf spring electrode which forms a protruding electrode 112; and a leaf spring sleeve which forms a protruding electrode housing portion 113. A portion of the leaf spring electrode also functions as a portion of an elastic member (none of these constitutional elements being indicated by symbols in the drawing).

According to the blood pump controller 3 of the modification 1, also in the mode where the electricity-receiving-side battery connection connector 110' on the housing inner side is surrounded by the waterproof partition wall 168, waterproof property of the inner circuit 164 can be further enhanced by providing the second sealing member 162.

(2-2) For example, it may be possible to provide a treatment where the connection between the electricity-receiving-side battery connection connector 110 and the inner circuit 164 is molded by a molding material 169 made of a resin or the like (modification 2).

Figure 7:
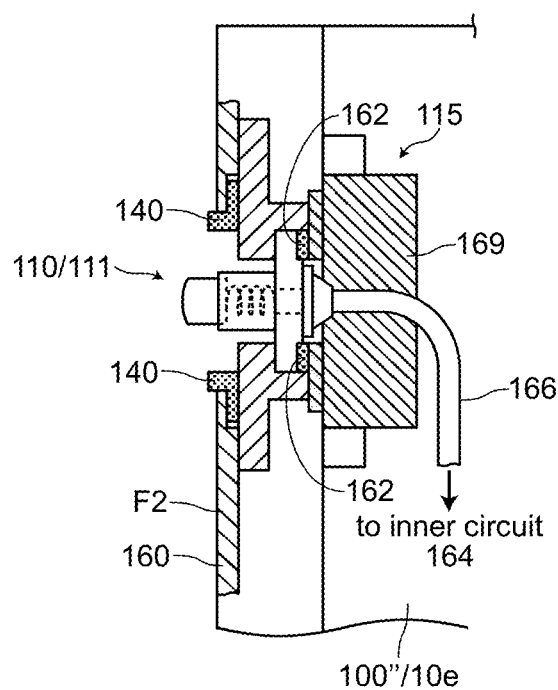
FIG. 7 is a cross sectional view of a blood pump controller 4 according to a modification 2.

FIG. 7 is a cross-sectional view of a blood pump controller 4 according to the modification 2. In FIG. 7, constitutional elements equal to the corresponding constitutional elements in the respective embodiments are indicated by the same symbols as the respective embodiments, and the description of the constitutional elements is omitted.

According to the blood pump controller 4 of the modification 2, by molding the connection between the electricity-receiving-side battery connection connector 110 and the inner circuit 164 by the molding material 169, it is possible to prevent intrusion of water from the electricity-receiving-side battery connection connector 110 itself and an area in the vicinity of the electricity-receiving-side battery connection connector 110 and hence, waterproof property of the inner circuit 164 can be further enhanced.

For a reference purpose, in the case of a blood pump controller, unlike general-use electronic equipment, for example, when remaining electricity stored in the battery pack is extremely small, there is a case where such a battery pack must be exchanged with a charged battery pack in any external environment. For example, a case is estimated where there is no way but to exchange the battery pack outside even when it is raining.

The controller where waterproof treatment is performed in the housing such as the blood pump controller 3 according to the modification 1, the blood pump controller 4 according to the modification 2 or the like can acquire higher waterproof property with certainty. Accordingly, even when the controller is used in the above-mentioned harsh external environment, a battery exchange can be performed more safely.

(3) In the respective embodiments, the second surface F2 of the slot 120 is approximately formed in a planar shape except for an area in the vicinity of the opening portion 127. However, the present invention is not limited to such a case. For example, a bottom portion of a portion of the case member 160 to which the first sealing member 140 is attached and an area in the vicinity of the portion may be raised from a bottom portion of the remaining portion of the case member 160 thus forming a mesa 126, and a surface of the mesa 126 may be formed as a second surface F2' of the present invention (modification 3).

Figure 8A:
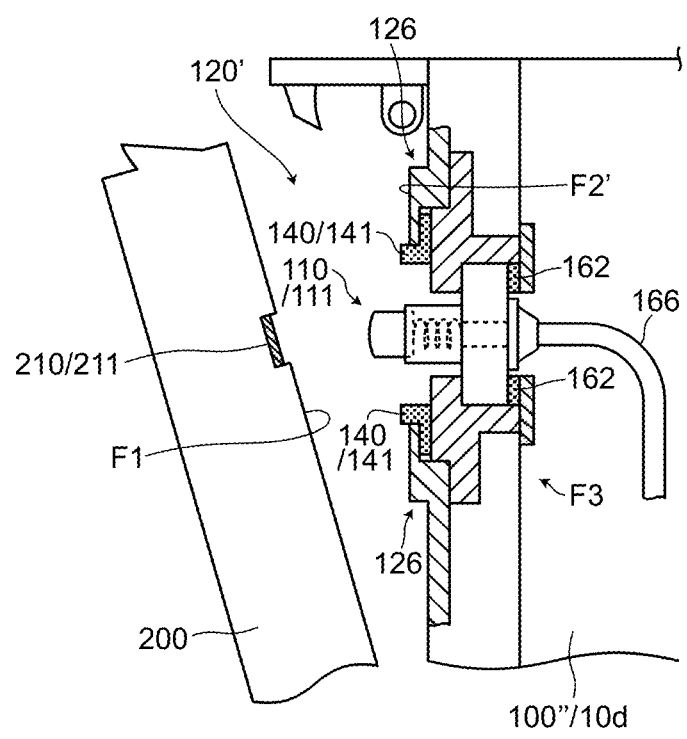
FIG. 8A and FIG. 8B are cross-sectional views of a main part of a blood pump controller 5 according to a modification 3.
Figure 8B:
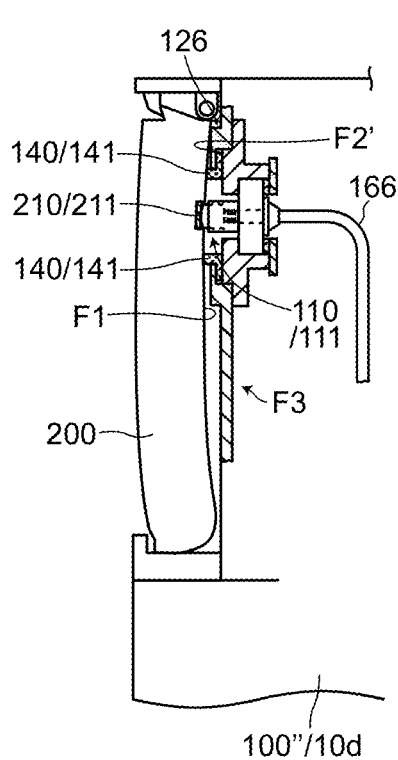
Figure 9:
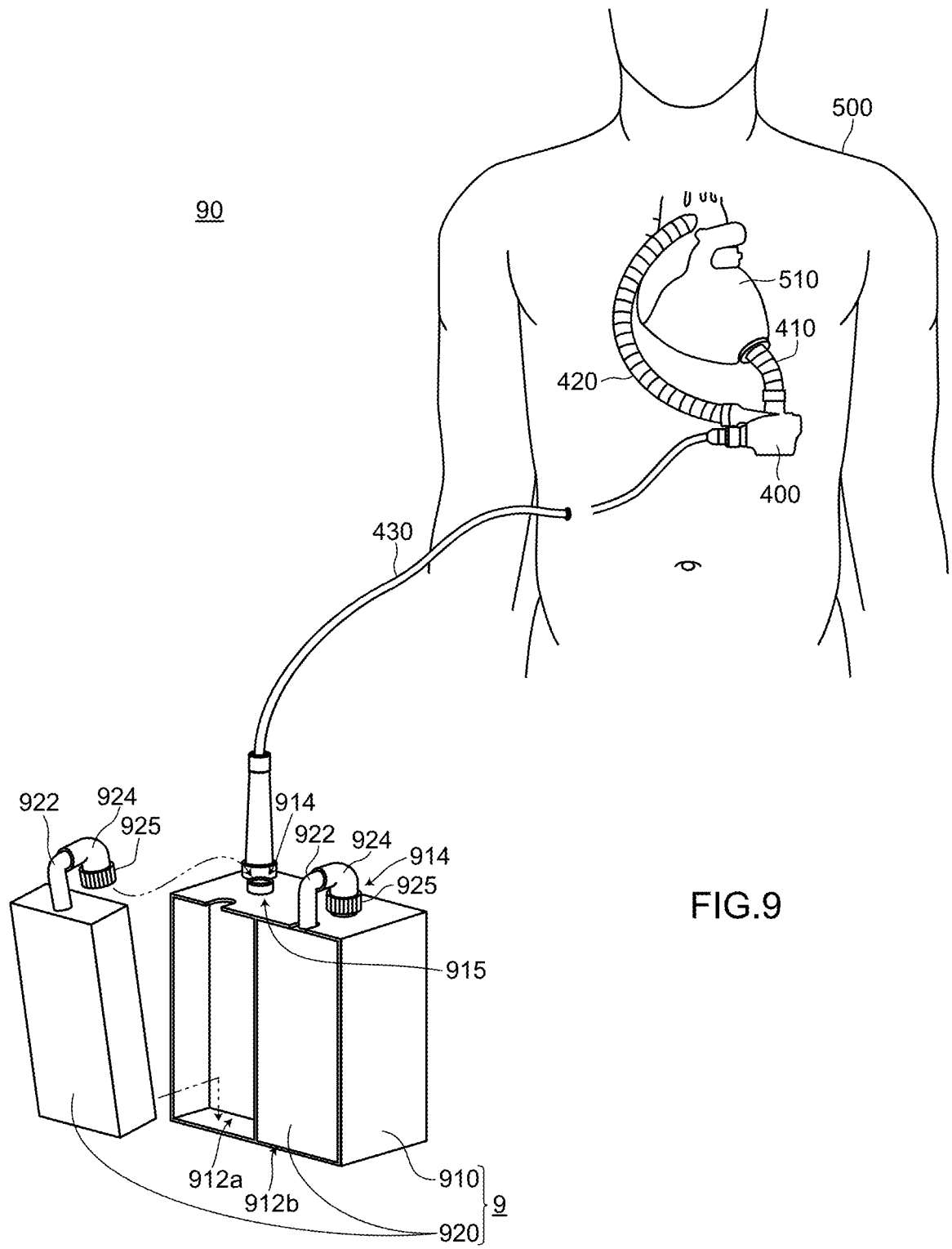
FIG. 9 is a view of a conventional blood pump controller 9 and a conventional ventricular assist system 90.
Figure 10A:
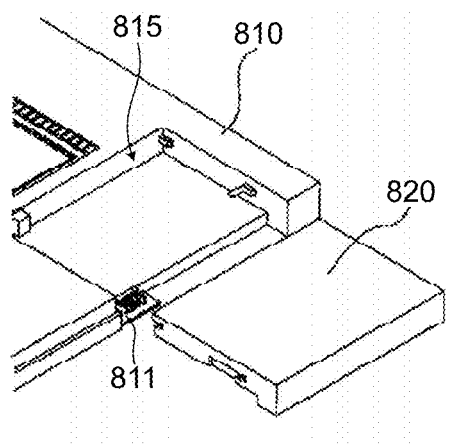
FIG. 10A to FIG. 10C are views of the connection structure between a battery pack 820 and a notebook PC 810 described in JP 2002-110287 A.
Figure 10B:
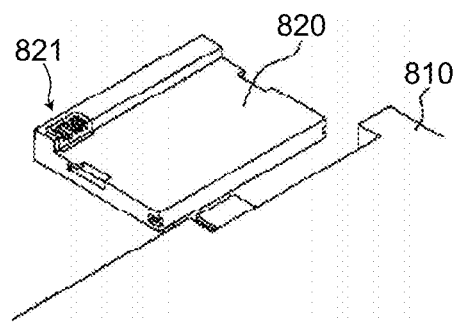
Figure 10C:
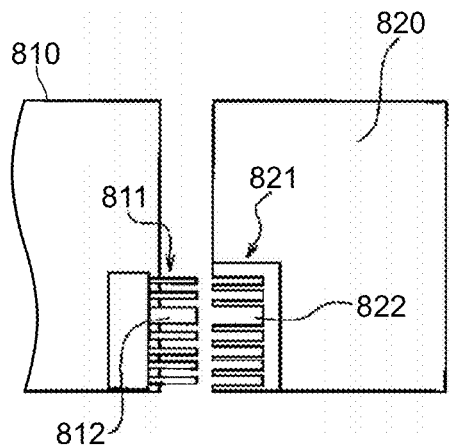

FIG. 8A and FIG. 8B are cross-sectional views of a main part of a blood pump controller 5 according to the modification 3. FIG. 8A shows a state where a battery pack 200' is about to be housed in a slot 120', and FIG. 2B shows a state where housing of the battery pack 200' in the slot 120' is finished.

According to the blood pump controller 5 of the modification 3, by forming the mesa 126 at the portion of the case member 160 and at the area in the vicinity of the portion where the second surface F2' of the slot 120' is formed by raising the bottom of the portion of the case member 160 from the bottom portion of the remaining portion of the case member 160, a height of the electrode of the electricity-receiving-side battery connection connector 110 and a height of the first sealing member 140 become larger than a height of the remaining portion by an amount corresponding to raising of the bottom. Accordingly, for example, even when the battery pack 200' is distorted, it is possible to acquire an electrical contact and connection with certainty and, at the same time, sealing by the first sealing member 140 can be performed.

(4) In the respective embodiments, the first sealing member 140 is attached to the "second surface F2" side so as to surround the electricity-receiving-side battery connection connector 110. However, the present invention is not limited to such a case. For example, although not shown in the drawings, the first sealing member 140 may be attached to the "first surface F1" side so as to surround the electricity-supply-side battery connection connector 210. The first sealing member may be attached to both the first surface F1 and the second surface F2.

(5) In the embodiments 1 to 3 and the modifications 2 and 3, the description has been made with respect to the case where, as the electricity-receiving-side battery connection connector 110, the spring type connector 111 having the pin-probe-shaped electrode which includes the plunger type electrode, the plunger barrel, and the spring coil is used. However, the present invention is not limited to such a case. For example, the leaf-spring-like spring type connector which is used in the modification 1 may be used in the embodiments 1 to 3, and the modifications 2 and 3. Further, the spring type connector having the pin-probe-shaped electrode which is used in the embodiments 1 to 3 and the modifications 2 and 3 may be used in the modification 1.

What is claimed is:

1. A blood pump controller configured to control a blood pump which takes a blood into a pump chamber and supplies the blood taken into the pump chamber into a body of a user by a blood supply mechanism, the blood pump controller comprising:
    a controller body connected to the blood pump by way of a drive cable and configured to drive the blood pump;
    a battery pack configured to store electricity and to supply stored electricity to the controller body; and
    a battery housing body having a slot in which the battery pack is housed and held, wherein
    the controller body is configured to function also as the battery housing body,
    the battery pack has at least a first surface on which an electricity-supply-side battery connection connector is disposed,
    the slot has at least a second surface on which an electricity-receiving-side battery connection connector is disposed,
    the battery pack and the battery housing body are configured such that, in a state where the battery pack is housed in the slot, an electrical connection is made between the electricity-supply-side battery connection connector and the electricity-receiving-side battery connection connector which form a pair of battery connection connectors, and the first surface and the second surface opposedly face each other,
    a first sealing member is attached to at least either one of the first surface or the second surface and is configured to provide sealing such that the first sealing member entirely surrounds and seals the pair of battery connection connectors in a state where the battery pack is housed in the slot and the first surface and the second surface opposedly face each other, and
    wherein the first sealing member comprises a first waterproof packing.

2. The blood pump controller according to claim 1, wherein either one of the electricity-supply-side battery connection connector or the electricity-receiving-side battery connection connector is formed of a spring type connector having a protruding electrode and a protruding electrode housing portion, and being capable of generating an elastic force which acts against a press fitting force when the protruding electrode is press-fitted in the protruding electrode housing portion, and
    assuming a height of the first waterproof packing in a state where a seal pressing force is not applied to the first waterproof packing as Hs using the first surface or the second surface to which the first waterproof packing is attached as a reference,
    assuming a height of a top portion of the protruding electrode in a state where the press fitting force is not applied as H1 using the first surface or the second surface to which the spring type connector is attached as a reference, and
    assuming a height of the top portion of the protruding electrode or a height of the spring type connector in a state where the top portion of the protruding electrode is brought into a deepest position by pressing by applying the press fitting force as H2 using the first surface or the second surface to which the spring type connector is attached as a reference,
    the spring type connector and the first waterproof packing are disposed so as to satisfy a relationship of $H2<Hs<H1$.

3. The blood pump controller according to claim 1, wherein a guide which guides a lower end protruding portion formed on a lower end of the battery pack is disposed on a slot lower portion which forms a lower portion of the slot, and
    a latching mechanism which engages with an upper end protruding portion formed on an upper end of the battery pack and latches an upper end side of the battery pack is disposed on a slot upper portion which forms an upper portion of the slot.

4. The blood pump controller according to claim 1, wherein the battery housing body further includes a second sealing member which provides waterproofing between an electrode side of the electricity-receiving-side battery connection connector and an inner circuit disposed in a housing of the battery housing body.

5. The blood pump controller according to claim 4, wherein a waterproof partition wall is further disposed in the housing of the battery housing body and is formed so as to surround a portion of the electricity-receiving-side battery connection connector on a housing inner side together with a third surface which is a surface of a case member forming the slot and being disposed on a side opposite to the second surface of the case member,
    one end of a wiring pattern is connected to the electricity-receiving-side battery connection connector on the housing inner side,
    the wiring pattern traverses the waterproof partition wall and is connected to the inner circuit, and
    the second sealing member which provides sealing between the waterproof partition wall and the wiring pattern is disposed in a transverse portion where the wiring pattern traverses the waterproof partition wall.

6. The blood pump controller according to claim 1, wherein in a case where the blood pump controller is operated in a battery drive mode, a cable of an electric system pulled out from the controller body to an outside is only the drive cable.

7. A ventricular assist system comprising:
a blood pump configured to take a blood into a pump chamber and supply the blood taken into the pump chamber into a body of a user by a blood supply mechanism;
a drive cable connected to the blood pump; and
a blood pump controller connected to the drive cable and configured to control the blood pump, wherein
the blood pump controller is the blood pump controller described in claim 1.

8. A blood pump controller configured to control a blood pump which takes a blood into a pump chamber and supplies the blood taken into the pump chamber into a body of a user by a blood supply mechanism, the blood pump controller comprising:
a controller body connected to the blood pump by way of a drive cable and configured to drive the blood pump;
a battery pack configured to store electricity and to supply stored electricity to the controller body; and
a battery housing body having a slot in which the battery pack is housed and held, wherein
the controller body and the battery housing body are connected to each other by a given connection cable,
the battery pack has at least a first surface on which an electricity-supply-side battery connection connector is disposed,
the slot has at least a second surface on which an electricity-receiving-side battery connection connector is disposed,
the battery pack and the battery housing body are configured such that, in a state where the battery pack is housed in the slot, an electrical connection is made between the electricity-supply-side battery connection connector and the electricity-receiving-side battery connection connector which form a pair of battery connection connectors, and the first surface and the second surface opposedly face each other,
a first sealing member is attached to at least either one of the first surface or the second surface and is configured to provide sealing such that the first sealing member entirely surrounds and seals the pair of battery connection connectors in a state where the battery pack is housed in the slot and the first surface and the second surface opposedly face each other, and
the first sealing member is formed of a first waterproof packing.

* * * * *